(12) United States Patent
Zarowitz et al.

(10) Patent No.: US 7,488,451 B2
(45) Date of Patent: Feb. 10, 2009

(54) SYSTEMS FOR PARTICLE MANIPULATION

(75) Inventors: Michael A. Zarowitz, San Carlos, CA (US); Glenn R. Edwards, Palo Alto, CA (US)

(73) Assignee: Millipore Corporation, Billerica, MA (US)

( * ) Notice: Subject to any disclaimer, the term of this patent is extended or adjusted under 35 U.S.C. 154(b) by 811 days.

(21) Appl. No.: 10/901,942

(22) Filed: Jul. 28, 2004

(65) Prior Publication Data
US 2005/0084423 A1   Apr. 21, 2005

Related U.S. Application Data

(60) Provisional application No. 60/537,454, filed on Jan. 15, 2004, provisional application No. 60/523,747, filed on Nov. 19, 2003.

(51) Int. Cl.
*G01N 35/10* (2006.01)
(52) U.S. Cl. .................. 422/67; 422/100; 422/101
(58) Field of Classification Search .................. 422/63, 422/67, 100, 101
See application file for complete search history.

(56) References Cited

U.S. PATENT DOCUMENTS

| | | |
|---|---|---|
| 3,772,099 A | 11/1973 | Ryan et al. |
| 3,897,284 A | 7/1975 | Livesay |
| 3,964,294 A | 6/1976 | Shair et al. |
| 4,053,433 A | 10/1977 | Lee |
| 4,131,064 A | 12/1978 | Ryan et al. |
| 4,197,104 A | 4/1980 | Krystyniak et al. |
| 4,329,393 A | 5/1982 | LaPerre et al. |
| 4,363,965 A | 12/1982 | Soberman et al. |
| 4,469,623 A | 9/1984 | Danielson et al. |
| 4,544,836 A | 10/1985 | Galvin et al. |
| 4,640,035 A | 2/1987 | Kind et al. |
| 4,652,395 A | 3/1987 | Marcina et al. |
| 4,768,858 A | 9/1988 | Hussein |
| 5,114,855 A | 5/1992 | Hu et al. |
| 5,143,854 A | 9/1992 | Pirrung et al. |
| 5,202,265 A | 4/1993 | LaMora |
| 5,364,557 A | 11/1994 | Faris |
| 5,409,839 A | 4/1995 | Balestrieri et al. |
| 5,451,505 A | 9/1995 | Dollinger |
| 5,563,583 A | 10/1996 | Brady et al. |
| 5,581,257 A | 12/1996 | Greene et al. |
| 5,591,592 A | 1/1997 | Ruoslahti et al. |
| 5,656,441 A | 8/1997 | Faller et al. |
| 5,674,698 A | 10/1997 | Zarling et al. |
| 5,688,696 A | 11/1997 | Lebl |

(Continued)

FOREIGN PATENT DOCUMENTS

GB    2 306 484 A    5/1997

(Continued)

OTHER PUBLICATIONS

Al-Mawlawi, D., et al., "Nanowires Formed in Anodic Oxide Nanotemplates," *J. Mater. Res.*, 9(4): 1014-1018 (1994).

(Continued)

*Primary Examiner*—Matthew O Savage
(74) *Attorney, Agent, or Firm*—Hamilton, Brook, Smith & Reynolds, P.C.

(57) ABSTRACT

Systems, including methods and apparatus, for particle manipulation to perform assays.

14 Claims, 11 Drawing Sheets

U.S. PATENT DOCUMENTS

| | | | |
|---|---|---|---|
| 5,708,153 A | 1/1998 | Dower et al. | |
| 5,710,038 A | 1/1998 | Mes-Masson et al. | |
| 5,741,462 A | 4/1998 | Nova et al. | |
| 5,744,305 A | 4/1998 | Fodor et al. | |
| 5,751,629 A | 5/1998 | Nova et al. | |
| 5,760,394 A | 6/1998 | Welle | |
| 5,770,455 A | 6/1998 | Cargill et al. | |
| 5,773,224 A | 6/1998 | Grandics et al. | |
| 5,786,626 A | 7/1998 | Brady et al. | |
| 5,817,751 A | 10/1998 | Szardenings et al. | |
| 5,840,485 A | 11/1998 | Lebl et al. | |
| 5,846,719 A | 12/1998 | Brenner et al. | |
| 5,874,214 A | 2/1999 | Nova et al. | |
| 5,874,724 A | 2/1999 | Cato | |
| 5,919,706 A * | 7/1999 | Tajima | 436/54 |
| 5,925,562 A | 7/1999 | Nova et al. | |
| 5,961,923 A | 10/1999 | Nova et al. | |
| 5,981,166 A | 11/1999 | Mandecki | |
| 5,981,180 A | 11/1999 | Chandler et al. | |
| 5,989,835 A | 11/1999 | Dunlay et al. | |
| 5,990,479 A | 11/1999 | Weiss et al. | |
| 6,017,496 A | 1/2000 | Nova et al. | |
| 6,018,299 A | 1/2000 | Eberhardt | |
| 6,023,540 A | 2/2000 | Walt et al. | |
| 6,025,129 A | 2/2000 | Nova et al. | |
| 6,025,200 A | 2/2000 | Kaish et al. | |
| 6,046,003 A | 4/2000 | Mandecki | |
| 6,051,377 A | 4/2000 | Mandecki | |
| 6,075,134 A | 6/2000 | Bertozzi et al. | |
| 6,083,693 A | 7/2000 | Nandabalan et al. | |
| 6,083,763 A | 7/2000 | Balch | |
| 6,087,186 A | 7/2000 | Cargill et al. | |
| 6,093,370 A | 7/2000 | Yasuda et al. | |
| 6,100,026 A | 8/2000 | Nova et al. | |
| 6,100,973 A | 8/2000 | Lawandy | |
| 6,103,479 A | 8/2000 | Taylor | |
| 6,104,038 A | 8/2000 | Gonzalez et al. | |
| 6,114,038 A | 9/2000 | Castro et al. | |
| 6,129,896 A | 10/2000 | Noonan et al. | |
| 6,133,030 A | 10/2000 | Bhatia et al. | |
| 6,136,251 A | 10/2000 | Etzbach et al. | |
| 6,136,274 A | 10/2000 | Nova et al. | |
| 6,184,035 B1 | 2/2001 | Csete et al. | |
| 6,207,770 B1 | 3/2001 | Coates et al. | |
| 6,210,910 B1 | 4/2001 | Walt et al. | |
| 6,214,560 B1 | 4/2001 | Yguerabide et al. | |
| 6,225,112 B1 | 5/2001 | Sakai et al. | |
| 6,238,869 B1 | 5/2001 | Kris et al. | |
| 6,251,691 B1 | 6/2001 | Seul | |
| 6,274,323 B1 | 8/2001 | Bruchez et al. | |
| 6,296,189 B1 | 10/2001 | Lawandy et al. | |
| 6,306,975 B1 | 10/2001 | Zhao et al. | |
| 6,319,668 B1 | 11/2001 | Nova et al. | |
| 6,326,144 B1 | 12/2001 | Bawendi et al. | |
| 6,395,555 B1 | 5/2002 | Wilson et al. | |
| 6,406,840 B1 | 6/2002 | Li et al. | |
| 6,441,901 B2 | 8/2002 | McFarland et al. | |
| 6,458,937 B1 | 10/2002 | Bertozzi et al. | |
| 6,534,307 B1 | 3/2003 | Muraca | |
| 6,643,001 B1 | 11/2003 | Faris | |
| 6,752,490 B2 | 6/2004 | Pickrell | |
| 6,828,157 B1 | 12/2004 | Pankowsky | |
| 6,887,431 B1 * | 5/2005 | Vann et al. | 506/43 |
| 6,908,737 B2 | 6/2005 | Ravkin et al. | |
| 6,977,152 B2 | 12/2005 | Foulkes et al. | |
| 7,225,082 B1 | 5/2007 | Natan et al. | |
| 7,253,435 B2 | 8/2007 | Siniaguine et al. | |
| 2001/0049101 A1 | 12/2001 | Brogger et al. | |
| 2002/0123078 A1 | 9/2002 | Seul et al. | |
| 2002/0137059 A1 | 9/2002 | Wu et al. | |
| 2002/0165179 A1 | 11/2002 | Baker | |
| 2002/0197656 A1 | 12/2002 | Li et al. | |
| 2003/0007152 A1 | 1/2003 | McFarland et al. | |
| 2003/0008323 A1 | 1/2003 | Ravkin et al. | |
| 2003/0017445 A1 | 1/2003 | Berg et al. | |
| 2003/0059764 A1 | 3/2003 | Ravkin et al. | |
| 2003/0104494 A1 | 6/2003 | Ravkin et al. | |
| 2003/0129654 A1 | 7/2003 | Ravkin et al. | |
| 2003/0134330 A1 | 7/2003 | Ravkin et al. | |
| 2003/0157730 A1 | 8/2003 | Walker et al. | |
| 2003/0166015 A1 | 9/2003 | Zarowitz et al. | |
| 2003/0170744 A1 | 9/2003 | Beske | |
| 2003/0207249 A1 | 11/2003 | Beske et al. | |
| 2003/0219800 A1 | 11/2003 | Beske et al. | |
| 2004/0018485 A1 | 1/2004 | Ravkin et al. | |
| 2004/0038306 A1 | 2/2004 | Agnew et al. | |
| 2004/0126773 A1 | 7/2004 | Beske et al. | |
| 2005/0009113 A1 | 1/2005 | Goldbard et al. | |
| 2005/0084914 A1 | 4/2005 | Foulkes et al. | |
| 2005/0208468 A1 | 9/2005 | Beske et al. | |
| 2007/0273789 A1 | 11/2007 | Siniaguine et al. | |

FOREIGN PATENT DOCUMENTS

| | | |
|---|---|---|
| WO | WO 83/01308 A1 | 4/1983 |
| WO | WO 96/36436 A1 | 11/1996 |
| WO | WO 97/03931 A1 | 2/1997 |
| WO | WO 97/12680 A2 | 4/1997 |
| WO | WO 97/20074 A1 | 6/1997 |
| WO | WO 97/35201 A1 | 9/1997 |
| WO | WO 98/37417 A1 | 8/1998 |
| WO | WO 98/38490 A1 | 9/1998 |
| WO | WO 98/46550 A1 | 10/1998 |
| WO | WO 98/53093 A1 | 11/1998 |
| WO | WO 99/13313 A1 | 3/1999 |
| WO | WO 99/19515 A1 | 4/1999 |
| WO | WO 99/19711 A1 | 4/1999 |
| WO | WO 99/22018 A2 | 5/1999 |
| WO | WO 99/36564 A1 | 7/1999 |
| WO | WO 99/37814 A1 | 7/1999 |
| WO | WO 99/41006 A1 | 8/1999 |
| WO | WO 99/67641 A2 | 12/1999 |
| WO | WO 00/00145 A2 | 1/2000 |
| WO | WO 00/16893 A2 | 3/2000 |
| WO | WO 00/22435 A1 | 4/2000 |
| WO | WO 00/32542 A1 | 6/2000 |
| WO | WO 00/33079 A1 | 6/2000 |
| WO | WO 00/39587 A1 | 7/2000 |
| WO | WO 00/61281 A1 | 10/2000 |
| WO | WO 00/63419 A1 | 10/2000 |
| WO | WO 00/63695 | 10/2000 |
| WO | WO 00/73777 A1 | 12/2000 |
| WO | WO 01/20015 A1 | 3/2001 |
| WO | WO 01/25002 A1 | 4/2001 |
| WO | WO 01/25510 A1 | 4/2001 |
| WO | WO 01/26038 A1 | 4/2001 |
| WO | WO 01/51207 A1 | 7/2001 |
| WO | WO 01/61040 A1 | 8/2001 |
| WO | WO 01/62699 A1 | 8/2001 |
| WO | WO 01/77391 A1 | 10/2001 |
| WO | WO 01/77678 A1 | 10/2001 |
| WO | WO 01/78288 A2 | 10/2001 |
| WO | WO 01/89585 A1 | 11/2001 |
| WO | WO 01/96604 A2 | 12/2001 |
| WO | WO 01/98765 A1 | 12/2001 |
| WO | WO 02/37944 A2 | 5/2002 |
| WO | WO 03/018760 A2 | 3/2003 |
| WO | WO 2004/034012 A2 | 4/2004 |
| WO | WO 2005/028621 A2 | 3/2005 |

OTHER PUBLICATIONS

Amit, M., et al., "Human Feeder Layers for Human Embryonic Stem Cells," *Biology of Reproduction*, 68(6): 2150-2156 (2003).

Baselt, D., et al., "Biosensor Based on Force Microscope Technology," *J. Vac. Sci. Technol. B.*, 14(2): 789-793 (1996).

Berglund, D., et al., "A Rapid Analytical Technique for Flow Cytometric Analysis of Cell Viability Using Calcofluor White M2R," *Cytometry*, 8: 421-426 (1987).

Beske, O., et al., "High-throughput cell analysis using multiplexed array technologies," *Drug Discovery Today*, 7(18 Suppl.): S131-S135 (2002).

Björk, L., et al., "Computerized assessment of production of multiple human cytokines at the single-cell level using image analysis," *Journal of Leukocyte Biology*, 59(2): 287-295 (1996).

Blawas, A., et al., "Protein Patterning," *Biomaterials*, 19: 595-609 (1998).

Clark, A., et al., "Decreased Insulin Secretion in Type 2 Diabetes: A Problem of Cellular Mass or Function?," *Diabetes*, 50 (Suppl. 1): S169-S171 (Feb. 2001).

Czarnik, A., "Illuminating the SNP Genomic Code," *Modern Drug Discovery*, 1(2): 49-55 (1998).

Egner, B., et al., "Tagging in Combinatorial Chemistry: The Use of Coloured and Fluorescent Beads," *Chemical Communications*, pp. 735-736 (1997).

Final Conference Program of LabAutomation '98 held in San Diego, CA Jan. 17-21, 1998, pp. 99, 100, 124, and 129 [retrieved on Oct. 29, 2007]. Retrieved from the Internet <url: http://labautomation.org/confarchives.php>.

Frank, R., "Strategies and Techniques in Simultaneous Solid Phase Synthesis Based on the Segmentation of Membrane Type Supports," *Bioorganic & Medicinal Chemistry Letters*, 3(3): 425-430 (1993).

Fratamico, P., et al., "Detection of *Escherichia coli* O157:H7 using a surface plasmon resonance biosensor," *Biotechnology Techniques*, 12(7): 571-576 (1998).

Gupta, V., et al., "Optical Amplification of Ligand-Receptor Binding Using Liquid Crystals," *Science*, 279: 2077-2080 (1998).

Lam, K., et al., "A New Type of Synthetic Peptide Library for Identifying Ligand-Binding Activity," *Nature*, 354: 82-84 (1991).

Lee, J., et al., "Engineering Novel Cell Surface Receptors for Virus-Mediated Gene Transfer," *The Journal of Biological Chemistry*, 274(31): 21878-21884 (1999).

Mahal, L., et al., "Engineering Chemical Reactivity on Cell Surfaces Through Oligosaccharide Biosynthesis," *Science*, 276: 1125-1128 (1997).

Martens, C., et al., "A Generic Particle-Based Nonradioactive Homogeneous Multiplex Method for High-Throughput Screening Using Microvolume Fluorimetry," *Analytical Biochemistry*, 273(1): 20-31 (1999).

Martin, B., et al., "Orthogonal Self-Assembly on Colloidal Gold-Platinum Nanorods," *Adv. Mater.*, 11(12): 1021-1025 (1999).

Martin, C., "Membrane-Based Synthesis of Nanomaterials," *Chem. Mater.*, 8(8): 1739-1746 (1996).

McNeish, J., "Embryonic Stem Cells in Drug Discovery," *Nature Reviews, Drug Discovery*, 3: 70-80 (2004).

Mendelsohn, J., et al., "Rational Design of Cytophilic and Cytophobic Polyelectrolyte Multilayer Thin Films," *Biomacromolecules*, 4(1): 96-106 (2003).

Mohr, S., et al., "Microarrays as Cancer Keys: An Array of Possibilities," *Journal of Clinical Oncology*, 20(14): 3165-3175 (2002).

Needels, M., et al., "Generation and Screening of an Oligonucleotide-Encoded Synthetic Peptide Library," *Proc. Natl. Acad. Sci. USA*, 90: 10700-10704 (1993).

Rowe, C., et al., "Array Biosensor for Simultaneous Identification of Bacterial, Viral, and Protein Analytes," *Analytical Chemistry*, 71(17): 3846-3852 (1999).

Specifications microtiter plates of Micronit Microfluidics B.V., pp. 1-2; [retrieved on Oct. 29, 2007]. Retrieved from the Internet <url: http://www.micronit.com/en/products/standard_glass_chips/microtiter_plate.php>.

*Symposium BB Nonlithographic Methods for Organizing Materials into Functional Structures*, pp. 1-9, Nov. 30-Dec. 2, 1998.

*Symposium C-Anisotropic Nanoparticles—Synthesis, Characterization, and Applications*, pp. 54-69, Nov. 27-29, 2000.

Torrance, C., et al., "Use of Isogenic Human Cancer Cells for High-throughput Screening and Drug Discovery," *Nature Biotechnology*, 19: 940-945 (2001).

*Webster's II New Riverside University Dictionary*, Houghton Mifflin Company, pp. 126 and 760 (1994).

Yarema, K., et al., "Metabolic Delivery of Ketone Groups to Sialic Acid Residues," *The Journal of Biological Chemistry*, 273(47): 31168-31179 (1998).

Ziauddin, Junaid, and Sabatini, David M., "Microarrays of Cells Expressing Defined cDNAs," *Nature*, 411: 107-110 (2001).

Gown, A., et al., "Improved Detection of Apoptotic Cells in Archival Paraffin Sections: Immunohistochemistry Using Antibodies to Cleaved Caspase 3," *The Journal of Histochemistry & Cytochemistry*, 50(4): 449-454 (2002).

Furst, A., et al. "Rapid Immunofluorescent Screening Procedure Using Primary Cell Cultures or Tissue Sections," Journal of Immunological Methods, 70: 101-109, 1984.

Hodder, P., et al. "A Flow Injection Renewable Surface Technique for Cell-Based Drug Discovery Functional Assays," Anat. Chem., 71: 1160-1166, 1999.

* cited by examiner

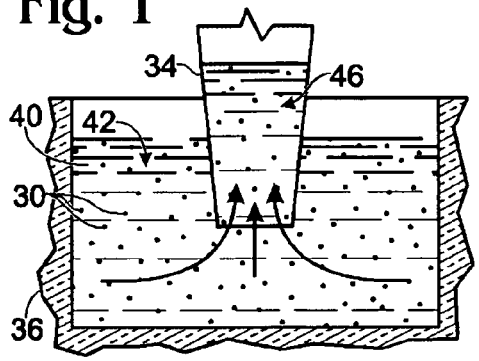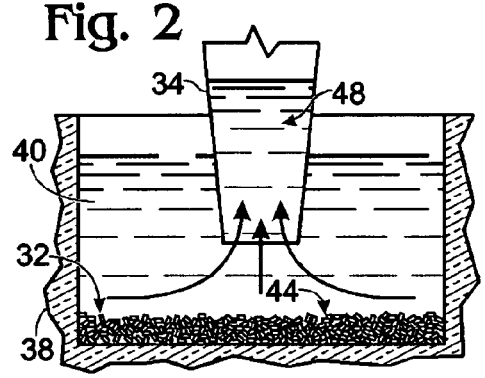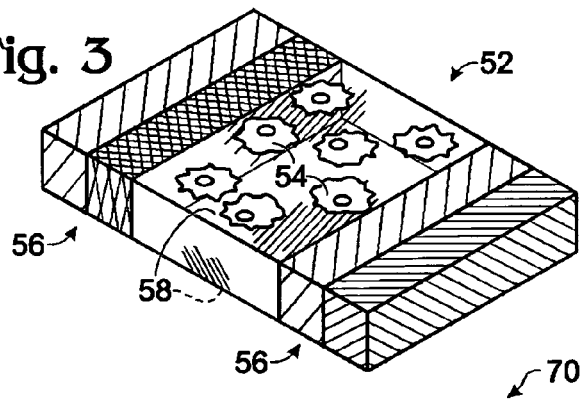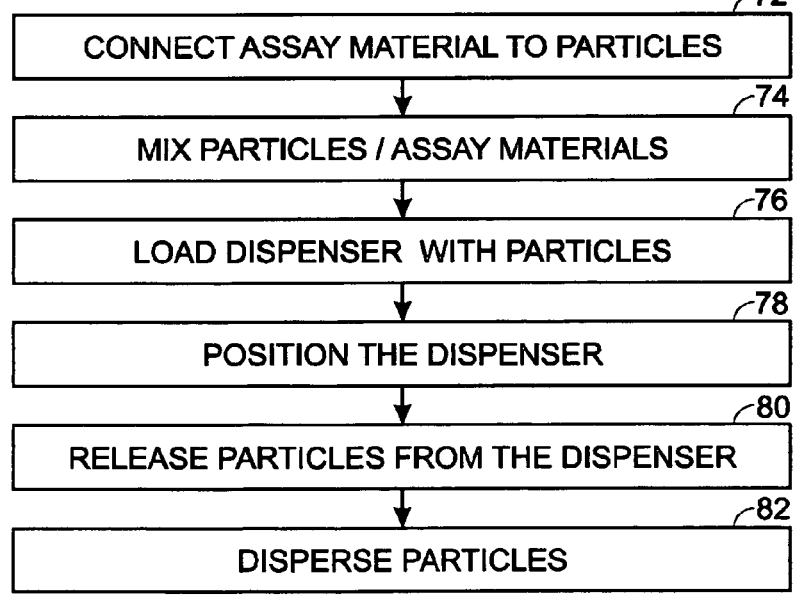

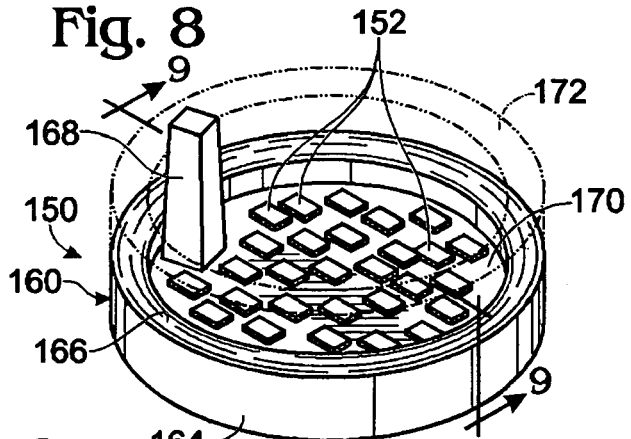
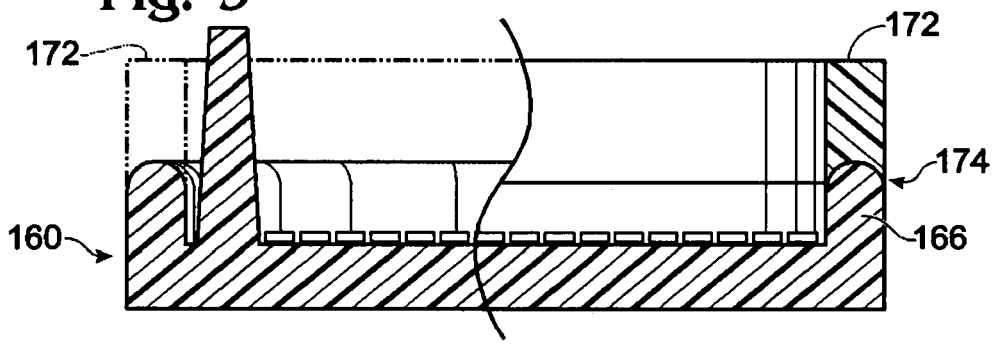
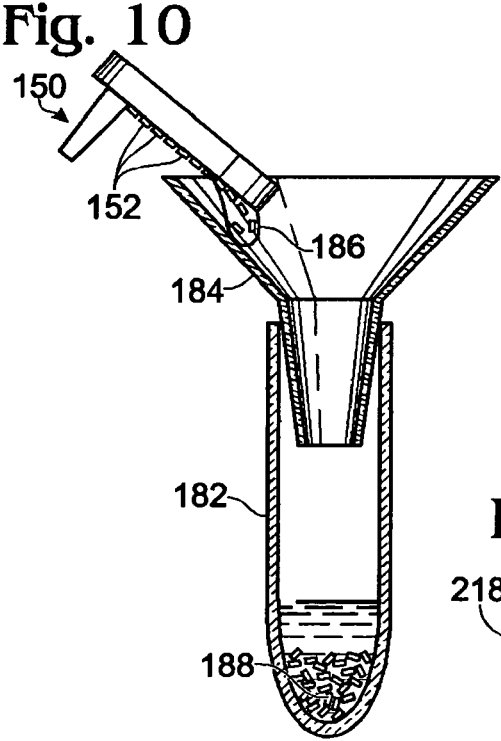
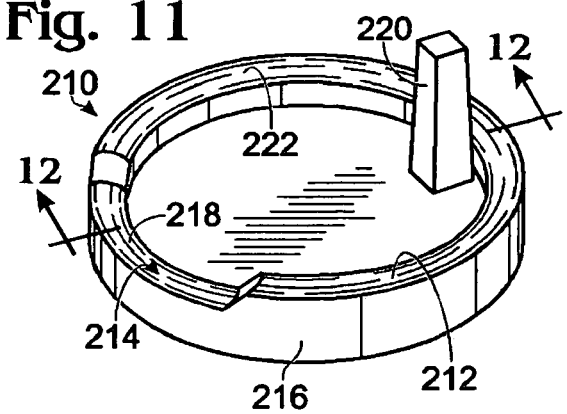
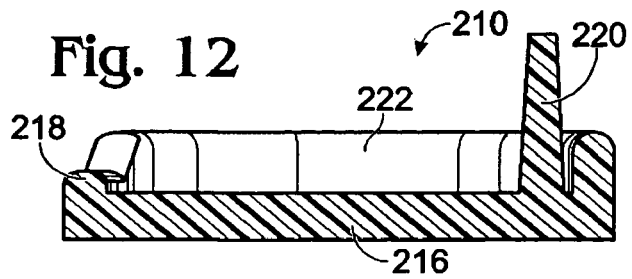

SYSTEMS FOR PARTICLE MANIPULATION

CROSS-REFERENCES TO PRIORITY APPLICATIONS

This application is based upon and claims the benefit under 35 U.S.C. § 119(e) of the following U.S. provisional patent applications, which are incorporated by reference in their entirety for all purposes: Ser. No. 60/523,747, filed Nov. 19, 2003; and Ser. No. 60/537,454, filed Jan. 15, 2004.

CROSS-REFERENCES TO RELATED APPLICATIONS

This application incorporates by reference in their entirety for all purposes the following U.S. patent applications: Ser. No. 09/549,970, filed Apr. 14, 2000; Ser. No. 09/694,077, filed Oct. 19, 2000; Ser. No. 10/120,900, filed Apr. 10, 2002; Ser. No. 10/238,914, filed Sep. 9, 2002; Ser. No. 10/273,605, filed Oct. 18, 2002; Ser. No. 10/282,904, filed Oct. 28, 2002; Ser. No. 10/282,940, filed Oct. 28, 2002; Ser. No. 10/382,796, filed Mar. 5, 2003; Ser. No. 10/382,797, filed Mar. 5, 2003; Ser. No. 10/382,818, filed Mar. 5, 2003; Ser. No. 10/407,630, filed Apr. 4, 2003; Ser. No. 10/444,573, filed May 23, 2003; Ser. No. 10/445,291, filed May 23, 2003; Ser. No. 10/713,866, filed Nov. 14, 2003; and Ser. No. 10/842,954, filed May 10, 2004.

This application also incorporates by reference in its entirety for all purposes the following U.S. provisional patent application: Ser. No. 60/503,406, filed Sep. 15, 2003.

INTRODUCTION

Particles may be used in various assays, particularly biological assays. For example, particles may be configured as carriers of assay materials, such as samples and/or associated reagents. However, the nonfluidic behavior of particles may provide substantial challenges to automated and/or manual manipulation of these particles. For example, it may be difficult to dispense particles reproducibly to microplate wells to perform high throughput assays.

SUMMARY OF THE INVENTION

The present teachings provide systems, including methods and apparatus, for particle manipulation to perform assays.

BRIEF DESCRIPTION OF THE DRAWINGS

FIG. 1 is a fragmentary view of a pipet disposed in a suspended configuration of smaller particles in fluid, with the pipet receiving a portion of the fluid and a corresponding portion of the smaller particles, in accordance with aspects of the present teachings.

FIG. 2 is a fragmentary view of a pipet disposed in fluid above a sedimented configuration of larger particles, with the pipet receiving a portion of the fluid and no larger particles, in accordance with aspects of the present teachings.

FIG. 3 is a view of an exemplary particle that may be suitable for manipulation by the systems of the present teachings to perform assays.

FIG. 4 is a flowchart of an exemplary method of dispensing particles that may be performed in part or completely by the systems of the present teachings.

FIG. 8 is a view of one of the exemplary transfer platforms of FIG. 6 supporting a plurality of particles in the absence of the sample holder, in accordance with aspects of the present teachings.

FIG. 9 is a sectional view of the transfer platform of FIG. 8, taken generally along line 9-9 of FIG. 8.

FIG. 10 is a partially sectional view of one of the transfer platforms of FIG. 6 positioned above a funnel and a vessel, with the transfer platform inverted, so that the particles are traveling from the transfer platform, through the funnel, toward fluid disposed in the bottom of the vessel.

FIG. 11 is a view of another example of a transfer platform for supporting a plurality of particles, in accordance with aspects of the present teachings.

FIG. 12 is a sectional view of the transfer platform of FIG. 11, taken generally along line 12-12 of FIG. 11.

DETAILED DESCRIPTION

Figure 5:
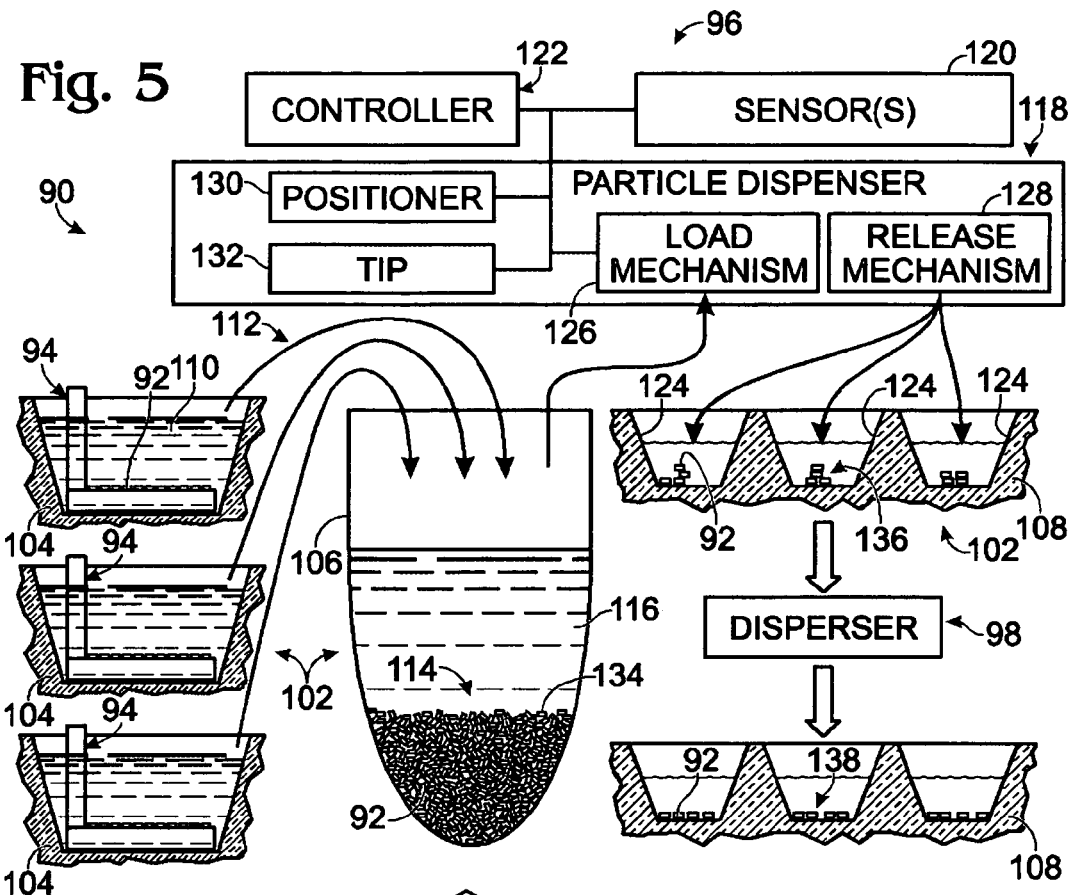
FIG. 5 is a somewhat schematic view of an exemplary system for dispensing particles, in accordance with aspects of the present teachings.

Systems, including methods and apparatus, are provided for particle manipulation to perform assays. The particle manipulation may include (1) supporting and/or arraying the particles for connection to assay materials, such as samples and/or reagents; (2) transferring of particles and their connected assay materials to a particle supply; (3) dispensing subsets of the particles from the particle supply to assay (receiving) sites, such as microplate wells; and/or (4) dispersing of the subsets of the particles at the assay sites, among others. Accordingly, the apparatus may include (1) a transfer device, such as a platform or ladle, for supporting and/or arraying the particles and for transferring the particles from a connection site to the particle supply, (2) a dispensing system for automatically dispensing aliquots of particles from the particle supply to assay sites, and/or (3) a dispersion apparatus for spreading the particles out on a surface, such as a surface of the assay sites. The present teachings may provide more efficient manipulation of particles for biological assays, for example, faster and/or more reproducible dispensing of particles to assay sites, less damaging dispensing of particles and assay materials (such as cells), and/or higher percentages of nonoverlapping dispensed particles at assay sites (and thus more assay data), among others.

Further aspects of the present teachings are described in the following sections: (I) exemplary effects of particle properties on particle manipulation; (II) overview of exemplary systems for particle manipulation; (Ill) particles; (IV) assay materials; (V) particle dispensers, including (A) loading mechanisms, (B) release mechanisms, (C) positioners, and (D) supply sites and receiving sites; (VI) sensors; (VII) controllers; (VIII) particle dispersion; and (IX) examples.

I. EXEMPLARY EFFECTS OF PARTICLE PROPERTIES ON PARTICLE MANIPULATION

Properties of particles, such as their size, shape, and/or composition, among others, may determine the behavior of the particles in fluid. FIGS. 1 and 2 illustrate how two exemplary sizes of particles, smaller particles 30 and larger particles 32, may provide different challenges to their automated transfer with a fluid transfer device, such as a pipet 34, from their respective vessels 36, 38. Particles 30, 32 may be of similar densities and more dense than a fluid 40 in which they are disposed, so that smaller particles 30 sediment more slowly than larger particles 32 in the fluid. Accordingly, smaller particles 30 may provide a suspended particle configuration 42, and larger particles 32 may provide a sedimented or settled particle configuration 44, at comparable times after suspension of the particles in the fluid. These different particle configurations may provide different challenges to their automated (or manual) transfer with the pipet. Alternatively, or in addition, the particles may have different densities that affect their transfer with the pipet. For example, plastic beads may settle more slowly than glass beads of comparable size.

FIG. 1 shows that smaller particles 30 may be transferred more consistently with pipet 34. In particular, smaller particles 30 may form a more stable suspension in fluid 40 than larger particles 32 (see FIG. 2), with the smaller particles in a more persistent fluid-borne state and in a relatively uniform distribution. Accordingly, a portion of fluid 40 loaded into pipet 34 from first vessel 36, shown at 46 in FIG. 1, should have a corresponding portion of the particles 30. Furthermore, if the smaller particles sediment slowly enough, successive fluid aliquots of similar volume loaded into pipet 34 should include similar numbers of the smaller particles.

FIG. 2 illustrates how larger particles 32 may be transferred inconsistently with pipet 34. In particular, larger particles 32 may settle quickly after suspension in the fluid 40, so that these larger particles are not uniformly distributed in the fluid. As a result, a portion of fluid 40 loaded into the pipet 34 from the second vessel 38, shown at 48 in FIG. 2, may not include a corresponding portion of the larger particles 32. In addition, successive aliquots with similar volumes of the fluid each may have no particles or widely varying numbers of the particles, determined, for example, by the position of the pipet tip relative to the settled particles during uptake of each fluid aliquot into the pipet. Furthermore, the consistency/uniformity of particle transfer generally decreases as the particle size increases relative to the size of the conveyance (such as the pipet volume). Accordingly, assays that rely on the presence of larger particles 32 may yield inconsistent results.

FIG. 3 shows an exemplary particle 52 that may be suitable for manipulation by the systems of the present teachings. Particle 52 may be larger, for example, because it is configured to carry cells 54 to assay sites. Furthermore, particle 52 may be configured as a coded carrier by including a detectable code 56, which may identify the cells 54, such as according to their type. Particle 52 may be generally flat, with generally planar, opposing surfaces 58 to permit, for example, optical analysis of cells 54 or subcellular portions thereof. Further aspects of particles configured as coded carriers, are described below in Section III and in the patent applications incorporated by reference therein.

The shape of the particles may affect their manipulation. For example, nonspherical particles, such as particle 52 of FIG. 3, may present numerous challenges over spherical particles. In particular, such nonspherical particles may have planar surfaces that restrict or bias reorientational motion of the particles and increase surface tension. Such particles thus may be unable to flow readily past one another. As a result, when particles near the top of a particle pile are removed from the pile, adjacent particles may not flow into the resulting cavity until the surface angle of the cavity equals or exceeds the maximum stable surface angle of the cavity, termed the angle of repose. The angle of repose may be different for each particle configuration. Accordingly, the particles may form semi-stable stacks of particles that are resistant to lateral motion and have local variations in height. In addition, nonspherical particles may present distinct and varying cross-sections, surface orientations, and flow characteristics as they tumble in a fluid flow. Also, nonspherical particles may have "up" and "down" orientations when they carry a sample (such as cells) asymmetrically on the particles (such as on one of two opposing surfaces). Furthermore, nonspherical particles may include edges that damage one another or assay materials, especially cells, that are connected to the particles. Moreover, larger nonspherical particles may have an increased response to gravity relative to surface tension, but may be strongly affected by surface tension effects. Larger forces and/or higher fluid flow rates thus may be necessary to lift many types of nonspherical particles from a settled configuration. Accordingly, greater shear forces may be created that separate assay materials, such as cells, from the particles. As a further potential complication, nonspherical particles may be more resistant to dispersion into a tiled or monolayer configuration after delivery to an assay site.

A pipet tip may be difficult to position properly relative to settled nonspherical particles. In particular, these particles may have a heterogeneous packing configuration and a mass sufficient to necessitate that the pipet tip be very close to the particles so that fluid flow into the pipet lifts the particles along with the fluid. For example, if the particles are too far from the pipet tip, as shown in FIG. 2, then fluid flow may not result in efficient and/or consistent co-transfer of particles. In contrast, if the pipet tip is positioned in contact with the particles, this contact may compress the particles together, to provide less effective co-transfer of particles with fluid moving into the pipet tip and/or may break the particles.

Release of loaded nonspherical particles from the pipet into a receiving site, such as a microplate well, also may be problematic. For example, the resistance of nonspherical particles to fluid flow and the relatively high flow rates that may be required to load particles into the pipet, may produce particle aggregates in which the particles are wedged in the pipet. In addition, with hard and/or sharp particles, such as particles formed of glass, edges or corner of the particles may cut into a softer material forming a wall of the pipet, to inhibit particle release.

II. OVERVIEW OF EXEMPLARY SYSTEMS FOR PARTICLE MANIPULATION

This section provides an overview of exemplary systems, including methods and apparatus, for particle manipulation; see FIGS. 4 and 5.

A. Exemplary Method

FIG. 4 shows a flowchart of an exemplary method 70 of particle manipulation for biological assays. The steps presented here may be performed in any suitable combination, in any suitable order, any suitable number of times, including once, twice, or more than twice, in parallel and/or serially. Additional and/or alternative steps also may be included in the method, as suggested below and elsewhere in the present teachings.

Method 70 may include a step of connecting assay materials to particles, shown at 72. The step of connecting may be performed to associate different sets (classes) of particles with different assay materials, for example, separate association of each set of particles with a different sample so that a code of each set identifies the different sample. Assay materials may include any material to be included in assays. Exemplary assay materials may include cells, such as cells of different types connected to different classes of particles having different identifying codes. In some examples, the assay materials may include reagents for analyzing samples. Further aspects of assay materials are described below in Section IV. Further aspects of connecting assay materials to particles are included in the patent applications listed above under Cross-References, which are incorporated herein by reference, particularly U.S. patent application Ser. No. 10/120,900, filed Apr. 10, 2002; U.S. patent application Ser. No. 10/382,797, filed Mar. 5, 2003; and U.S. patent application Ser. No. 10/407,630, filed Apr. 4, 2003.

Method 70 may include a step of mixing particles and their connected assay materials, shown at 74. Accordingly, the step of mixing may be performed after the step of connecting assay materials, so that the assay materials remain associated with their respective particles (and codes) after mixing. Mixing may include a step of combining different classes of particles so that the different classes can be mixed. The steps of connecting and/or combining may be facilitated with a transfer platform or ladle, such as one or more of the exemplary transfer platforms shown in FIGS. 6-12 and described, for example, below in Example 1 of Section IX. In some embodiments, particles may not be mixed at all or not until they have been dispensed to a receiving site. For example, particles of different classes may be dispensed to a well separately or as sub-mixtures of two or more classes.

Method 70 may include a step of loading a dispenser with particles, shown at 76. The step of loading may be based on fluid flow. Accordingly, the step of loading also may move a volume of fluid into the dispenser. Alternatively, or in addition, the step of loading may be based on an engagement of the particles with the dispenser, such as by scooping particles and/or forming an attraction between the particles and the dispenser, among others. The step of loading may be configured to load a predefined amount of particles. The predefined amount may correspond to an average number and/or average volume of particles, among others. The average number and/or average volume may have a standard deviation low enough to provide reproducible particle loading, for example, a standard deviation that is about one-half or one-fourth or one-tenth the average number/volume, among others. Loading may be performed with a mixture of particles/assay materials or with a single class of particles/assay materials, among others. During loading, the particles may be held by a supply site or particle reservoir, in the presence or absence of fluid.

Method 70 may include a step of positioning the dispenser, shown at 78. Positioning may be performed by horizontal and/or vertical movement of the dispenser, and particularly a tip of the dispenser. Positioning may be performed after loading the dispenser, for example, to move the dispenser between the supply site (a particle reservoir) and a receiving site (an assay site, such as a microplate well). Alternatively, or in addition, positioning may be performed before and/or during the step of loading, for example, to position the tip of the dispenser above the supply site and to bring this tip into the supply site at an appropriate vertical (and/or horizontal) position adjacent the particles in the supply site. In some examples, positioning of the dispenser may be performed by moving the supply and receiving sites, alternatively or in addition to moving the dispenser. Positioning along a vertical axis may be performed according to a calculated vertical position of a particle supply and/or based on a sensed vertical position of the particle supply, among others.

Method 70 may include a step of releasing particles from the dispenser, shown at 80. The step of releasing may be performed before, during, and/or after positioning the dispenser in and/or above the receiving site. The step of releasing may place a predefined amount of particles in the receiving site. Particle release may be performed in any suitable manner, for example, by moving fluid from the dispenser, re-orienting (such as tilting) the dispenser, removing an attraction between the dispenser and particles, and/or adding a repulsion between the dispenser and particles, among others. Loading and release of particles may have a one-to-one correspondence, that is, most or all of the particles loaded may be released to a receiving site. Alternatively, the step of loading may load enough particles for a plurality of receiving sites, so that the step of releasing delivers less than all of the loaded particles to each of two or more of these receiving sites after each loading operation. In other examples, loading may be performed a plurality of times for each release operation. In some examples, different classes of particles may be released separately (at the same time or at different times) to a receiving site.

Method 70 may include at step of dispersing particles, shown at 82. Particle dispersion may be performed to spread out particles on a surface, for example, before the step of connecting a sample to particles and/or after the step of releasing the particles to the receiving site.

B. Exemplary Apparatus

FIG. 5 shows an exemplary system 90 for manipulation of particles 92 to perform biological assays. Manipulation system 90 may include transfer devices or ladles 94; a particle dispensing system 96; a disperser 98; and suitable vessels 102, such as wells 104, tube(s)/flasks 106, microplates 108, and/or the like, for holding the particles; among others.

Transfer devices 94, also termed transfer platforms or ladles, may provide a support surface for the particles. For example, in the present illustration, each transfer platform 94 may hold particles 92, as cells or other assay materials are attached to the particles in a connection fluid 110 and/or while the assay materials are incubated with the particles (such as during cell culture). Alternatively, or in addition, each transfer platform 94 may be configured to permit the particles to be moved from wells 104 into tube 106, shown at 112, either manually or automatically, to create a particle mixture or particle supply 114, generally disposed in a supply fluid 116. Connection and supply fluids 110, 116 may be similar or different. In some examples, these fluids may include a culture medium to maintain cell viability.

Particle dispensing system 96 may be configured to dispense aliquots of particles 92 from particle supply 114 to receiving sites, such as wells of microplates 108. The particle dispensing system 96 may include, but is not limited to, a particle dispenser 118, a sensor(s) 120, and/or a controller 122, among others.

Particle dispenser 118 may be configured to move particles between particle supply 114 and receiving sites 124 of sample holders 108. Accordingly, particle dispenser 118 may include a loading mechanism 126 to bring particles into association with dispenser 118, in or adjacent particle supply 114, and a release mechanism 128 to reverse this association with the dispenser at receiving sites 124. Furthermore, particle dispenser 118 may include a positioner 130 configured to position a dispenser tip (a load/release interface) 132 of dispenser 118 suitably relative to particle supply 114 and to receiving sites 124. Positioner 130 may position the dispenser by moving the dispenser tip before, during, and/or after the loading and release operations.

Sensor 120 may be configured to sense positional information about particle supply 114 and/or dispenser interface 132. In some examples, this positional information may relate to the vertical position of the particle supply 114, particularly a top surface 134 of the particle supply. In some examples, this positional information may relate to the vertical spacing between particle supply and the dispenser tip. Dispensing system 96 alternatively or additionally may include one or more other sensors for sensing any other suitable aspects of the system.

Controller 122 may be configured to provide automated control of particle dispensing. Alternatively, or in addition, the controller may control connection of assay materials to particles, transfer of particles into tube 106, dispersion of particles after dispensing (see below), addition of reagents to any of the vessels 102, sensing of assay results, and/or the like. Accordingly, system 90 also may include one or more robotic devices to manipulate the vessels 102 or transfer platforms 94; fluid transfer devices to add fluid to, and/or remove fluid from, any of the vessels 102; detection mechanisms to measure experimental results; and/or the like. Any devices and/or mechanisms within a particle manipulation system may be coupled to the controller (and/or other (e.g., dedicated) controllers and/or to each other), for example, by electrical, optical, mechanical, or other suitable linkages, to provide coordinate operation and control of the manipulation system using the controller.

Disperser 98 may be configured to disperse particles from a less uniformly distributed, piled configuration, shown at 136, to a more uniformly distributed, tiled configuration, shown at 138.

III. PARTICLES

Particles generally comprise any small, discrete bodies included in assays. The particles may have any suitable size, shape, composition, and identifying features, and typically will be used as carriers to support samples and/or other materials during assays.

The particles may have any suitable size. The size may be selected, for example, based on the size of assay materials to be connected to the particles, the number of different classes of particles to be analyzed in a mixture, the size of a vessel (such as a microplate well) in which the particles will be assayed, the configuration of the dispensing system, and/or the like. In some examples, the particles may be sized so that two or more particles can be disposed together at an assay site, such as in a nonoverlapping arrangement on a surface. In some examples, the particles may be sized so that two or more particles can be viewed at once in a microscopic field of view. For example, the particles may be less than about 5 mm, or less than about 1 mm, in length or diameter or other characteristic dimension. In some examples, the particles may have a minimum size of at least about one micrometer. In an exemplary embodiment, intended for illustration only and not to restrict the size of the particles, the particles may be sized so that about 10-200 particles can fit in a substantially non-overlapping arrangement on the surface of a well of a standard 96-well microplate.

The particles may have any suitable shape, such as spherical or nonspherical. In some examples, the particles may be generally flat or planar, for example, with a pair of generally parallel opposing surfaces. In some embodiments, particles may be spherical, ovalloid, cubic, polyhedral, and/or the like. In some examples, the particles may have an aspect ratio such that they generally come to rest on one of two opposing faces, to increase the probability of an appropriate face being accessible by an imaging system.

The particles may be formed of any suitable material or materials, based, for example, on optical properties, biocompatibility, suitability for manufacturing, and/or so on. In some examples, the particles may be formed at least partially or at least substantially of glass and/or plastic. In some examples, the particles may be biological particles, such as cells or fragments thereof, among others. In some examples, the particles may have a composition, size, and shape such that they settle out of a fluid in which they are dispensed. The particles may settle in fluid so that the particles are removed from suspension, to rest on one another and/or on a vessel surface, among others. The particles may be configured to settle substantially in a time suitable for performing a given assay, or step thereof, for example, in less than about one hour, in less than about ten minutes or in less than about one minute, depending on the application.

The particles may include a code as a feature to identify each particle in a particle mixture, and thus to identify different assay materials associated with the particles at each assay site. The code may be positional and/or nonpositional. Furthermore, the code may be restricted to a coding portion of the particles or may be formed by at least substantially all of each particle. The code may be optically detectable.

Further aspects of particles, including suitable sizes, shapes, compositions, surface features, codes and methods of reading codes, mixtures, and the like, are included in the patent applications listed above under Cross-References, which are incorporated herein by reference, particularly the following U.S. patent applications: Ser. No. 09/549,970, filed Apr. 14, 2000; Ser. No. 09/694,077, filed Oct. 19, 2000; Ser. No. 10/120,900, filed Apr. 10, 2002; and Ser. No. 10/273,605, filed Oct. 18, 2002.

IV. ASSAY MATERIALS

Particles may be connected to assay materials before, during, and/or after the particles are dispensed to assay sites. The assay materials generally comprise any samples and/or reagents that may participate in and/or report on an assay. Exemplary samples and/or reagents may include cells (such as animal cells, plant cells, fungi, yeast, and/or bacteria, among others), cell extracts or fragments, viruses, vesicles, fluid samples (such as blood, mucous, semen, lymph, urine, a clinical aspirate, etc.), nucleic acids, proteins, peptides, carbohydrates, lipids, drug candidates, antibodies, receptors, ligands, small molecules, and/or the like. The assay materials may be connected covalently and/or noncovalently to particles. In some examples, the particles may correspond to the assay materials, such as when cells or cell aggregates (for example, tissue fragments/sections) are used as particles.

Further aspects of assay materials and methods of connecting assay materials to particles are described in the patent applications listed above under Cross-References, which are incorporated herein by reference, particularly U.S. patent application Ser. No. 10/407,630, filed Apr. 4, 2003.

V. PARTICLE DISPENSERS

Particle dispensers generally include any suitable devices for transferring particles from a particle supply to one or more receiving sites. In some examples, the particle dispensers may be configured to transfer predefined amounts (e.g., numbers of particles or volumes of particle suspensions), within an acceptable range of variation. Particle dispensers may include one or more loading mechanisms, release mechanisms, and/or positioners, for transfer between supply and receiving sites, as described further below.

A. Loading Mechanisms

A dispenser may have one or more loading mechanisms with which to load particles from a supply site, so that the dispenser retains the particles. Loading may be conducted with the particles partially or completely immersed in fluid, or in the absence of fluid, using any suitable mechanism.

With fluid present, loading may be conducted by flow of the fluid into the dispenser, so that the particles are co-loaded by fluid movement. Accordingly, during loading, fluid may be pushed, pulled (drawn), and/or poured, among others, into a fluid compartment of the dispenser. Pushing and/or pulling fluid may be performed with a pump (such as a syringe, piston, bellows, double-diaphragm, flexible impeller, gear, oscillating, progressing cavity, rotary, and/or peristaltic pump, among others). Alternatively, or in addition, the fluid may be drawn into the dispenser by capillary action and/or a pressurized gas, or poured in with the assistance of gravity.

Alternatively, or in addition, loading may be performed by providing an attractive force between the particles and the dispenser. The attractive force may be, for example, a magnetic attraction between a transfer interface of the dispenser, such as a tip of the dispenser, and the particles. Accordingly, the particles may include a magnetic material, and the dispenser and/or the particles may have a magnetic property that is selectively actuable, such as by supplying current to an electromagnet.

In some examples, loading may be performed in the absence of fluid. Loading without fluid may be performed, for example, by placing the particles in engagement with a support structure (such as a scoop, pincers, etc.). These mechanisms also or alternatively may be used in the presence of fluid.

The loading mechanism may define a compartment into which the particles are received and retained and from which the particles are released. The compartment may be at least substantially closed, such as a conduit or a chamber, or a region defined adjacent a surface. In some examples, the size of the compartment may determine the amount of particles that are loaded, such as by the average number/volume of particles that can fit into the compartment. For example, with magnetic attraction, the surface area of the dispenser that is magnetic may define the size of the compartment and thus the number/volume of particles loaded. With fluid flow, the volume of a compartment in which the particles are retained may limit and determine the number/volume of particles loaded, based, for example, on the average density with which the particles are packed in the compartment.

B. Release Mechanisms

A dispenser may include one or more release mechanisms with which to release loaded particles at a receiving site. The release mechanisms may operate by any suitable mechanism, for example, fluid flow, contact with a delivery site surface, positive displacement, removal of an attraction between the dispenser and loaded particles, and/or addition of a repulsion between the dispenser and loaded particles, among others.

Release by fluid flow may involve movement of fluid through a region of the dispenser. The direction of this movement may be opposite to a direction in which particles and fluid were loaded into the dispenser. Alternatively, or in addition, this movement may be in the same direction as particle/fluid loading, for example, particles/fluid added to a dispenser conduit from a first end, such as by pouring or pipetting, and then pushed from a generally opposing second end of the conduit.

In some examples, fluid may be moved alternately in opposing directions, to promote, for example, loosening of particles disposed in a tip of the dispenser. Such inward-outward movement may be performed any suitable number of cycles, including once, twice, thrice, or more. Movement or flow of fluid may be promoted by operation of a pump, such as one of those described above.

Movement and/or separation of fluid from the tip, alternatively or additionally, may be induced by contact of fluid in the tip or pendant from the tip, with a (solid or liquid) surface of the receiving site, for example, by bringing the tip or a pendant drop into contact with the surface and then pulling the tip away from the surface. With this type of fluid movement, the movement or separation of fluid from the tip may be assisted by fluid surface tension. A tip and/or its pendant drop(s) may be contacted with the surface any suitable number of cycles, including once, twice, thrice, or more. In some examples, inward-outward fluid may be followed by contact of the tip or its fluid with a receiving site surface and/or vice versa, and these combinations of operations may be repeated any suitable number of times, including once, twice, thrice, or more.

A subset or at least substantially all of the loaded particles may be released at the receiving site. Accordingly, in some embodiments, the step of loading may load enough particles for delivery to a plurality of receiving sites, and the step of releasing may be conducted at each of the receiving sites without reloading the dispenser. As a result, similar (or different) portions of the loaded particles may be released at each receiving site, for example, by selective displacement of a portion of the fluid and particles that were loaded into the dispenser.

C. Positioners

A positioner may include any mechanism for adjusting the position(s) of the dispenser relative to the supply site and/or receiving sites. Accordingly, the positioner may move the dispenser, the supply site, and/or the receiving sites. In some examples, the positioner may move the dispenser as the supply and receiving sites remain stationary, may move the dispenser vertically and the supply and receiving sites horizontally into alignment with the dispenser, may move the dispenser and adjust the vertical position of the supply site as the receiving sites remain stationary, and/or so on.

The positioner may provide movement in any suitable directions. The positioner may provide vertical movement, to adjust the vertical position/spacing of the dispenser and/or supply/receiving sites, and side-to-side movement along one axis or orthogonal axes, to adjust the absolute and/or relative horizontal position/spacing of the dispenser, the supply site, and/or the receiving sites. The positioner may move along one axis at a time, or may move relative to two or more axes at once, to provide non axial movement that is linear or nonlinear. Alternatively, or in addition, the positioner may provide rotational/tilting movement of the dispenser (and/or a tip thereof), the supply site, and/or the receiving sites. The positioner may be configured to move the dispenser, the supply site, and/or the receiving sites between preset and/or calculated positions. Alternatively, or in addition, the positioner may operate at least partially based on a sensed position of the supply site, particles therein, the dispenser, and/or the receiving sites, among others.

The positioner may operate by any suitable electromechanical configuration. In exemplary embodiments, the positioner may include one or more rack-and-pinion interfaces, one or more electric motors, and/or the like.

D. Supply Sites and Receiving Sites

The dispenser may transfer particles between spaced sites, a supply site(s) and one or more receiving sites.

The supply site may be defined by any suitable compartment for supporting or holding the particles and, optionally, fluid. The compartment may be defined by a vessel such as a beaker, flask, test tube, tube, vial, microplate well, plate, etc., or by a surface. The vessel may be configured to support and/or contain the particles and may be configured to hold fluid. In some embodiments, the compartment may be a plurality of spaced compartments, for example, different wells of a microplate, different regions of a surface, a plurality of connected syringes, different vials, and/or the like.

The particles at the supply site may include a single class of particles, or a mixture of classes of particles. Accordingly, transferring particles may transfer a preformed mixture of the particles, or separate transfer of different classes of the particles to a receiving site may form a mixture. Particles at the supply site may be connected already to assay materials and/or configured to be connected to assay materials during and/or after transfer of the particles to receiving sites. In some examples, dispensing may be performed from a plurality of supply sites, with each supply site having the same or different contents/samples/particles.

Fluid at the supply site may have any suitable composition, including organic or inorganic fluid(s). In some embodiments the supply fluid may be an aqueous media, and may include any suitable salt(s), buffer(s), cell nutrients, growth factors, proteins, carbohydrates, amino acids, reporter moieties, residual organic solvent(s), etc. Accordingly, in some embodiments, the supply fluid may be a medium suitable for culturing cells.

The supply fluid, if present, may be present at any suitable volume. Typically, the supply fluid will at least substantially surround the particles, so that the particles at the supply site are at least substantially are covered by fluid. Accordingly, the fluid may serve a number of functions at the supply site and/or during transfer. For example, the fluid may function to promote stability or a desired configuration of assay materials connected to the particles, such as keeping cells alive, reducing protein denaturation or assay material oxidation, etc. Alternatively, or in addition, the fluid may be used to impart a force on the particles for co-transfer of particles with the fluid as a portion (or all) of the fluid is moved.

The density and/or viscosity of the supply fluid may be selected as appropriate. In some embodiments, the supply fluid density may be less than the density of particles, to facilitate settling of the particles in the supply fluid. In other embodiments, the supply fluid density may be approximately equal to the density of the particles, so that the particles settle slowly (or not at all). In yet other embodiments, the supply fluid density may be greater than the density of the particles to enable the particles to float in the supply fluid. In yet other embodiments, the system may contain two or more types of particles, and the relationship between the supply fluid density and the density of the two or more types of particles may be the same or different, to facilitate cotransfer, or to facilitate separation and separate transfer, respectively.

The density and/or viscosity of the supply fluid may be adjusted, for example, by addition of an additive, such as a salt, a synthetic polymer, or an organic fluid, among others, to increase or decrease the density and/or viscosity. In some embodiments, the supply fluid density and/or viscosity may be increased with one or more of such additives, to decrease the rate at which the particles settle in the fluid. The fluid viscosity may be decreased (or increased), for example, to facilitate particle movement within the fluid, reduce (or increase) shear forces on the particles, and/or reduce (or increase) surface tension, among others. The above modifications to the supply fluid may be made prior to or during a dispensing run.

The supply fluid may be replenished during a dispensing run. This may be performed as needed, periodically, or in a continual process, among others. Replenishment of the supply fluid may serve to facilitate loading particles in fluid and/or to maintain samples (such as cells) in the supply site.

The receiving sites may define one or more compartments for receiving the particles delivered to these sites. Each compartment may be included in a volume defined by a vessel or may be a region adjacent a surface, among others. Exemplary compartments may be defined by wells of a microplate (a microtiter plate), subdivisions (such as sub-wells) of a well of a microplate, tubes, and/or a generally planar structure (such as a microscope slide, a cover slip, a biochip, etc.), among others. Each compartment may be empty when the particles are delivered, or may already include fluid, other particles, cells, drugs, assay materials, etc.

VI. SENSORS

A particle manipulation system may include one or more sensors. The sensors may be coupled to a controller and/or coupled directly to other devices/mechanisms of the particle manipulation system. Input from the sensor(s) may be recorded and/or used for any suitable purpose, for example, as part of a feedback loop to effect a change in value of the aspect being sensed.

The system may include a sensor to sense any suitable aspects of the system. Such system aspects may include temperature, gas composition (for example, carbon dioxide content), an aspect of light or other electromagnetic radiation (for example, light intensity), and/or the like. Alternatively, or in addition, the system aspects may relate to fluid flow rate; fluid pressure; fluid volume; presence/absence of particles, fluid, or vessels; positions of one or more vessels; and/or the like. Alternatively, or in addition, the sensor may measure contact with a surface through conductance, capacitance, pressure, and/or optical changes, among others. The sensor may measure light, sound, electricity, magnetic field strength (and/or orientation), and/or pressure, among others. Accordingly, the sensor may be optical, sonic or ultrasonic, electrical, mechanical, magnetic, piezoelectric, and/or the like.

The sensor may sense an aspect of the relative position of the dispenser (and/or dispenser tip) and the supply site, particularly particles within the supply site. Accordingly, in some examples, the sensor may sense contact between particles and the dispenser, movement of the supply site as a result of this contact, a vertical spacing between the particles and the dispenser, pressure exerted by the supply site on a support, and/or the like.

The sensor may cooperate with the positioner to achieve suitable positions or position adjustments of the dispenser, and particularly a tip (an interface structure) of the dispenser. For example, the sensor may cooperate with the positioner to define whether the dispenser tip is positioned a suitable distance from the particles, and/or to adjust this distance during fluid or particle loading and/or release.

VII. CONTROLLERS

A particle manipulation system may include one or more controllers. A controller may be any mechanism for controlling operation, particularly automated operation, of the system. The controller may be configured to send control signals to mechanisms/devices of the particle manipulation system, to actuate and/or regulate their operation. The controller also may be configured to receive status or sensed information from these mechanisms/devices, so that further control signals from the controller can be based on this information. In some examples, the controller may employ one or more algorithms to calculate the timing, rate, extent, and/or direction of positioner movement (and thus dispenser movement) and/or the timing, flow rate, and/or direction of fluid movement into/out of the dispenser (such as by controller operation of a pump). In some examples, the algorithms may employ instructions, parameter values, and/or preferences supplied by a user of the system, as described below.

The controller may be configured to receive inputs, such as instructions, values, and/or preferences, from a person using the system and to provide implementation of the inputs with one or more of the other mechanisms/devices of the system. Exemplary controllers may be digital controllers corresponding to digital processing devices, such as personal computers, among others. As used herein, a digital controller includes a digital processor for performing manipulation of digital data, such as logic and arithmetic operations on the data, among others. Alternatively, or in addition, controllers may be at least partially analog in operation.

User inputs may be provided by any suitable input device and may correspond to any suitable information. The inputs may be sent to the controller through a user interface, such as a keyboard, mouse, touch screen, dials, etc.; downloaded as digital files from storage media (discs, tapes, etc.); and/or the like. Exemplary inputs may be instructions/preferences that specify positional or status information about the particle supply or supply site, receiving sites, and/or dispenser, among others; set volumes of fluid/numbers of particles to be transferred and/or fluid flow rates to and from the transfer device; define transfer rates; and/or specify movement of the dispenser; among others.

VIII. PARTICLE DISPERSION

The particle manipulation systems described herein may be configured to disperse particles. Particle dispersion may include any process that spreads particles more evenly across a surface or within a volume. Dispersing particles may provide one or more advantage for assays, including (1) less optical interference between adjacent carriers, (2) fewer overlapping carriers with obscured or unreadable codes, (3) better access of reagents to surfaces of the particles, and/or (4) more experimental results per assay site, among others.

Particle dispersion may be performed, for example, by exerting suitable forces on a vessel holding particles in a less dispersed or nondispersed configuration. In some examples, these forces may be produced by striking the vessel from two or more sides of the vessel. Alternatively, or in addition, these forces may be produced by moving the vessel along one or more paths so that the vessel (or a vessel holder) collides suddenly with (or suddenly contacts or impacts) at least one bumper or stop to stop the vessel's movement along the path(s). In some examples, the vessel may be moved in opposing directions along each of two linear paths disposed generally orthogonal to one another. In some examples, a first linear path may be defined by a first guide structure slidably coupled to a second guide structure defining a second linear path. The second guide structure may be slidably coupled to a support that moves in an orbital pattern. In some examples, the support may be a platform of an orbital shaker. Further aspects of particle dispersion are included below in Example 4.

IX. EXAMPLES

The following examples describe selected aspects and embodiments of the present teachings, including systems for particle manipulation. These examples and the various features and aspects thereof are included for illustration and are not intended to define or limit the entire scope of the present teachings.

Example 1

Exemplary Transfer Platforms

This example describes exemplary transfer platforms (or ladles) that may be included in systems of particle manipulation for transferring particles manually and/or automatically, and methods of using the transfer platforms to facilitate connecting assay materials to particles and/or to provide particle transfer to other vessels, such as supply sites; see FIGS. 6-12.

Figure 6:
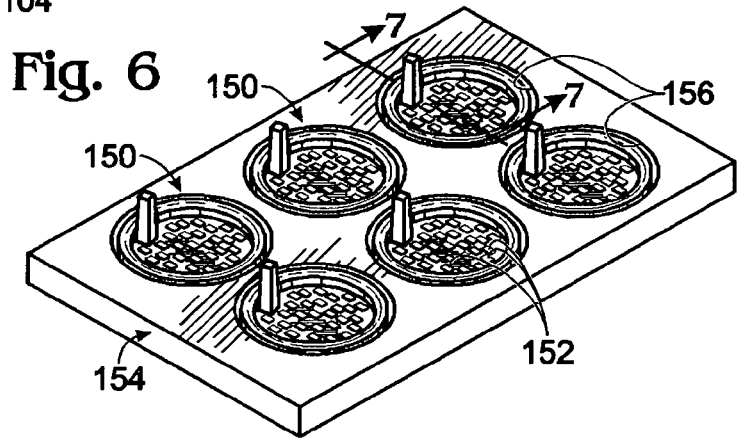
FIG. 6 is a view of a plurality of exemplary transfer platforms supporting particles in separate wells of a sample holder, in accordance with aspects of the present teachings.

FIG. 6 shows a plurality of exemplary transfer platforms 150 supporting particles 152 in a multi-well sample holder 154, particularly separate wells 156 of the holder, in accordance with aspects of the present teachings. The particles may be arrayed on the platforms and/or connected to assay materials, such as cells, while disposed on the platforms in the wells of sample holder 154. The transfer platforms and their particles then may be removed from the wells of the sample holder, and the particles and their connected assay materials transferred to another vessel via manipulation of the transfer platforms.

Figure 7:
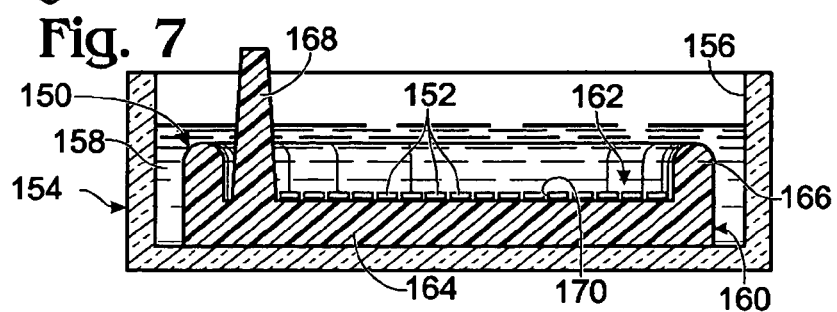
FIG. 7 is a sectional view of a transfer platform and a well from the sample holder of FIG. 6, taken generally along line 7-7 of FIG. 6.

FIG. 7 shows a sectional view of a transfer platform 150 disposed in a well 156 of the sample holder 154, taken generally along line 7-7 of FIG. 6. When disposed in the well, fluid 158 in the well may be added to a level that provides fluid communication between the particles 152 on the transfer platform and the well, as shown in the present illustration, or less fluid may be added so that there is no fluid communication between these particles and the well.

FIGS. 7 and 8 show aspects of the transfer platform 150. Transfer platform 150 may include a platform structure 160. The platform structure may provide a generally planar vessel or compartment 162 in which particles and fluid may be retained. The platform structure may include a base 164, and a wall or lip 166 joined to the base and extending generally upward there from. Platform also may include a handle 168 attached to the platform structure. Handle 168 may be configured to be engaged for movement of the platform structure. Platform structure 160 and handle 168 may be formed integrally or formed of two or more components that are coupled or secured to one another. The platform 160 and handle 168 may be formed of any suitable materials, including plastic, glass, metal, composite, and/or the like.

Base 164 may have any suitable structure. For example, the base may include a generally planar top surface 170 upon which particles 152 may be arrayed. The top surface 170 may be smooth or may have surface features, such as ridges/grooves, dimples, depression, and/or the like. These surface features may be configured, for example, to reduce surface tension and thus improve the ability of the particles to slide across the top surface. The base may have any suitable size and shape. In some examples, base 164 may be sized and shaped to fit into any suitable vessel, such as a tissue culture dish and/or a well of microplate, among others, such as a well of a six-well microplate/culture dish. Accordingly, the base 164 may be circular when viewed from the top, and thus shaped as a disk. The base 164 may be thick enough to provide sufficient strength to the platform structure, and thin enough for the base to fit completely into a suitable vessel.

Wall 166 may be configured as a retainer that restricts the ability of particles 152 to slide off the base 164. Accordingly, wall 166 may be configured as a lip that extends generally upward from the support surface 170, adjacent the perimeter of the support surface. Wall 166 may substantially or completely circumscribe support surface 170. In some examples, wall 166 may be configured as an annular lip disposed adjacent the perimeter of the base 164. Wall 166 may be continuous, as shown in the present illustration, or may include notches, perforations, and/or other openings through which fluid may pass to provide fluid communication between particles 152 in compartment 162 and fluid outward of the wall 166.

Handle 168 may have any suitable configuration. In some examples, the handle may be an engagement structure configured to be engaged by a tool or other suitable mechanical device, operated manually or automatically. Alternatively, or in addition, the handle may be configured to be engaged directly by hand, for example, between a finger(s) and thumb of a hand. The handle thus may be knurled or include other suitable surface structure, such as one or more ridges, grooves, depressions, projections, openings, and/or the like, configured, for example, to facilitate grasping the handle. Handle 168 may be joined to base 164 and/or wall 166, and may extend generally transverse from support surface 170, and thus generally upward from the platform structure 160 when the platform structure is resting on a horizontal surface. The handle may be generally linear, as shown in the present illustration, or may bend, for example, to reduce its height above the base. The handle may be long enough to extend above the top surface of sample holder 154, or may not extend upward this far (for example, so that the handle does not interfere with placement of a cover on the sample holder).

In some examples, platform structure 160 may include a removable barrier or wall extension 172, shown in FIGS. 8 and 9 in complete and partial phantom outline, respectively. Barrier 172 may be configured as a removable extension of an integrally formed wall 166, to increase the overall height of the wall and thus temporarily increase the volume of the compartment defined by the platform structure. Barrier 172 may be shaped similarly to integral wall 166, for example, annular in the present illustration. Barrier 172 may be configured to improve retention of particles and/or cells above the platform, to permit, for example, more vigorous movement of particles 152, platform structure 160, and/or added assay materials (such as cells), without causing the particles (or cells) to travel outside of integral wall 166. Alternatively, or in addition, the barrier 172 may be configured to restrict passage of fluid between integral wall 166 and barrier 172, to permit the platform structure 160 to be used without a surrounding vessel (such as well 156 of FIG. 7) during connection of assay materials to the particles. The barrier 172 thus may be configured to mate with integral wall 166, for example, as shown at 174 in FIG. 9. In some examples, the barrier 172 may extend inwardly adjacent the top of its wall portion, to form a cover or roof for the platform structure. In some cases, portion of the wall portion may be semi-permanent and thus easily removed or repositioned by a user to facilitate transfer of particles from the transfer platform. The cover may include an opening through which the handle 168 may extend, or the handle may fit under the cover or may be omitted. Removal of the barrier 172 may decrease the height of the retaining wall that circumscribes planar support surface 170 and thus may facilitate removal of the particles from the platform structure when they are being transferred.

FIG. 10 shows transfer platform 150 in an exemplary position for transfer of particles 152 to a vessel 182. Particles may be transferred directly into vessel 182. Alternatively, as shown in the present illustration, a funnel 184 may be disposed in the mouth of vessel 182 and/or above this vessel, effectively to widen the mouth of the vessel 182. Transfer platform 150 may be tilted and/or substantially inverted to promote movement of particles and fluid from the support surface of the transfer platform, shown at 186. Furthermore, the transfer platform may be positioned so its associated fluid contacts the funnel or the vessel (or a fluid disposed therein), to overcome surface tension and promote travel of the particles and the associated fluid into the vessel 182. In some examples, the tube may be filled with a fluid to a level accessible to the transfer platform, so that the transfer platform can contact the fluid directly, such as by partial or complete immersion of the transfer platform in the fluid, to overcome surface tension and promote particle separation from the transfer platform. Transferred particles may form part of a particle mixture or particle supply 188 from which particles may be dispensed to assay sites.

FIGS. 11 and 12 show another example of a transfer platform 210 for supporting a plurality of particles. Transfer platform 210 may include a wall 212 defining an opening or mouth 214 (an outlet) through which particles and associated fluid may be removed, for example, as shown in FIG. 10. Mouth 214 may have any suitable width and thus may extend along any suitable circumferential portion of the wall 212. Wall 212 may define mouth 214 by extending above base 216 to different heights. For example, a first wall region 218, generally opposing handle 220, may be shorter than a second wall region 222 extending around the base from the first wall region. Accordingly, the second wall region may provide more effective retention of particles on the base.

Transfer platforms may have any other suitable properties. Transfer platforms may be provided in a substantially sterile or nonsterile condition, as appropriate. For example, transfer platforms, or at least a platform structure thereof, may be provided in a sterile condition, for example, to reduce contamination of cells or other contamination-sensitive materials. A sterile condition, as used herein, is a condition achieved by purposeful treatment, such as exposure to heat, steam, irradiation, increased pressure, and/or a chemical, among others, to inactivate or kill microorganisms. The transfer platforms (or at least platform structures thereof) may be packaged individually or as sets, such as sets of six, among others. A package may be configured to at least substantially enclose one or more platform structure and/or transfer platforms. Transfer platforms may have any suitable size. In exemplary embodiments, intended for illustrative purposes, the base/platform structure may have a diameter of about 0.5-10 cm, and in particular exemplary embodiments, the diameter may be about two cm. In some exemplary embodiments, each transfer platform may be sized to hold enough particles to cover the bottom of about 10 wells of a 96-well microplate.

Example 2

Exemplary Dispensing Configurations

This example describes exemplary configurations that may be produced by an exemplary flow-based dispenser before, during, and/or after loading and releasing particles from the dispenser; see FIGS. 13-19.

Figures 13, 14, 15, 16, 17, 18:
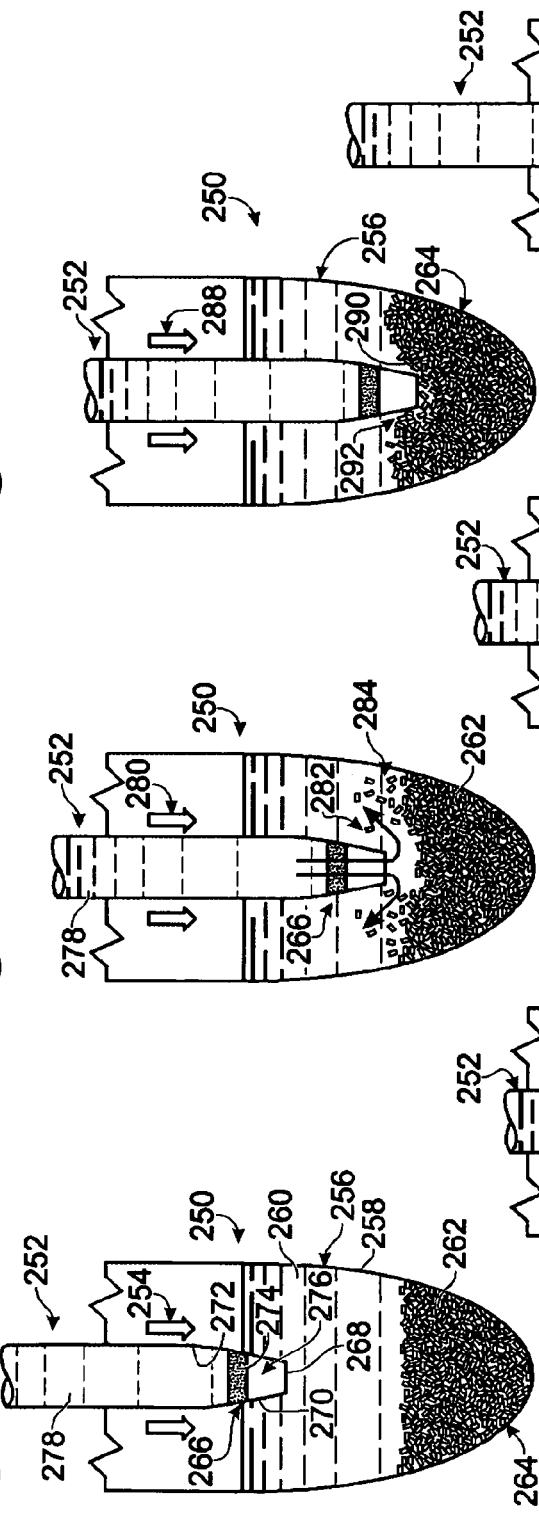
FIG. 13 is a fragmentary view of a dispenser and a vessel holding fluid and settled particles, with the dispenser entering the fluid and spaced from the settled particles, in accordance with aspects of the present teachings.
FIG. 14 is a fragmentary view of the dispenser and vessel of FIG. 13, with the dispenser approaching the particles while expelling fluid, so that a subset of the settled particles are fluidized and/or removed from the path of the dispenser, in accordance with aspects of the present teachings.
FIG. 15 is a fragmentary view of the dispenser and vessel of FIG. 13, with the dispenser contacting the settled particles, in accordance with aspects of the present teachings.
FIG. 16 is a fragmentary view of the dispenser and vessel of FIG. 13, with the dispenser drawing in fluid and a subset of the particles as the dispenser is traveling upward through the fluid, in accordance with aspects of the present teachings.
FIG. 17 is a fragmentary view of the dispenser and vessel of FIG. 13, with the dispenser loaded with particles and drawing in additional fluid as the dispenser is traveling upward from the settled particles, in accordance with aspects of the present teachings.
FIG. 18 is a fragmentary view of the dispenser and vessel of FIG. 13, with the dispenser traveling upward and about to separate from the fluid of the vessel, in accordance with aspects of the present teachings.

FIG. 13 shows a supply reservoir 250 and a portion of a dispenser 252 moving downward in the supply reservoir, shown at 254. In the present pre-loading configuration, dispenser 252 holds no particles. Movement of the dispenser may be controlled by a controller and/or a positioner, among others.

Supply reservoir 250 may include a vessel 256, such as a tube 258 with a closed bottom, holding a fluid (a "vessel fluid") 260 and particles 262. Particles 262 may be settled within the fluid, so that they are concentrated near the bottom of tube 258 to form a particle pile or particle supply 264.

Dispenser 252 may include a tip portion 266 having an opening 268 that defines a fluid interface (an inlet and/or outlet) for fluid travel from the dispenser to the vessel and/or from the vessel to the dispenser. The tip portion may include a wall 270 defining a conduit 272. The tip portion also may include a permeable member or filter 274 connected to the wall and configured to restrict movement of the particles through the conduit. Wall 270 and filter 274 thus may cooperatively define a loading space or volume 276 for the particles. Dispenser 252, and particularly tip portion 266, may hold a dispenser fluid 278 that is in fluid communication with vessel fluid 260. Accordingly, tip portion 266 may be pre-loaded with fluid before the tip portion enters vessel fluid 260. Alternatively, tip portion 266 may enter vessel fluid 260 without fluid in the tip portion initially. Dispenser fluid 278 may have a composition that is substantially the same as, or distinct from, vessel fluid 260.

FIG. 14 shows supply reservoir 250 with dispenser 252 still traveling downward, shown at 280, and closer to particles 262 than in the configuration of FIG. 13. Dispenser fluid 278 may be induced to flow outward from tip portion 266, shown at 282, for example, by the action of a pump included in the dispenser. The outward flow of dispenser fluid 278 may displace some particles, shown at 284, from the downward path of the tip portion. The displaced particles may re-settle laterally to the tip portion and/or may remain suspended during the loading operation. In some examples, this outward flow may be omitted and/or may be replaced by inward flow.

FIG. 15 shows supply reservoir 250 with dispenser 252 still traveling downward, shown at 288, and near an upper surface region 290 of particle pile 264, shown at 292. In some examples, the tip portion may be positioned within less than about one millimeter from the particle pile. In some examples, the tip portion may be positioned in contact with the particle pile. However, contact of the tip portion with the particle pile may damage the particle, their connected assay materials, and/or the tip portion. Accordingly, additional downward motion of the dispenser after contact with particle pile 264 may be coupled to corresponding downward movement of vessel 256 and/or corresponding upward movement of the tip portion (such as with a spring-loaded tip portion). In some examples, contact with the particle pile and/or downward movement of vessel 256 (or upward movement of the tip portion) resulting from such contact, may be sensed by a sensor, as described in more detail below in relation to FIGS. 24-27.

FIG. 16 shows supply reservoir 250 during loading of a portion of particles 262 and vessel fluid 260, shown at 302, into particle space 276 of the tip portion. Dispenser 252 may draw a portion of the vessel fluid 260 into the tip portion to induce particle movement along with fluid flow. Particle movement may be induced more effectively when the tip portion is positioned close to the particle pile. Accordingly, at some point during fluid intake, the tip portion may be disposed near and/or in contact with the particle pile. In some examples, the tip portion may be disposed within about one millimeter of the particle pile. Fluid intake by the dispenser may be initiated before the tip portion contacts the particle pile, after the tip portion contacts the particle pile, and/or before or after contact when the tip portion is within a predefined distance of the particle pile. The dispenser may remain stationary, may move upward, shown at 304, or may move downward, as the dispenser draws fluid and particles into the tip portion.

Upward movement of the dispenser, and/or positioning the tip portion close, but not in contact with the particle pile, may form a gap 306 between the particle pile and the tip portion, through which fluid may travel at a higher velocity. Although not wishing to be bound by theory, the higher velocity of fluid flow through this gap may produce a lower pressure, through a Venturi effect and according to Bernoulli's principle, thereby lifting adjacent particles from the particle pile and into the fluid flow stream. The fluid may travel through filter 274, shown at 308, but the particles may be retained by the filter in the particle space 276. In some examples, the fluid intake may be sufficient to at least substantially fill particle space 276 with packed particles, so that a predefined amount (number and/or volume) of particles is loaded into the dispenser. Additional particles may be retained by the dispenser during loading, for example, below the particle space to form a particle "beard." These additional particles may contribute to variation in the actual number/volume of particles loaded/transferred relative to the predefined amount of particles expected to be loaded and transferred. In some examples, the particle space may be partially loaded while the dispenser tip is in contact with the particle pile and then loading may be completed soon after the tip separates from the particle pile.

FIG. 17 shows supply reservoir 250 after loading particle space 276 to capacity with particles. Tip portion 266 may continue to travel upward, shown at 310, to further separate the tip portion from the particle pile. Fluid intake into the tip portion from the vessel fluid 260, relative to particle loading (FIG. 16), may be continued or stopped. When fluid intake is continued, the fluid may be drawn into the tip portion at any suitable flow rate, such as at a flow rate that is reduced, increased, or unchanged.

FIG. 18 shows supply reservoir 250 with dispenser 252 traveling upward, shown at 312, and about to leave the vessel fluid 260. Vessel fluid may be drawn into the tip portion at this point, shown at 314. This fluid inflow may counter effects of surface tension as the tip portion separates from the vessel fluid, for example, so that particle loss from the particle space is reduced or avoided.

Figure 19:
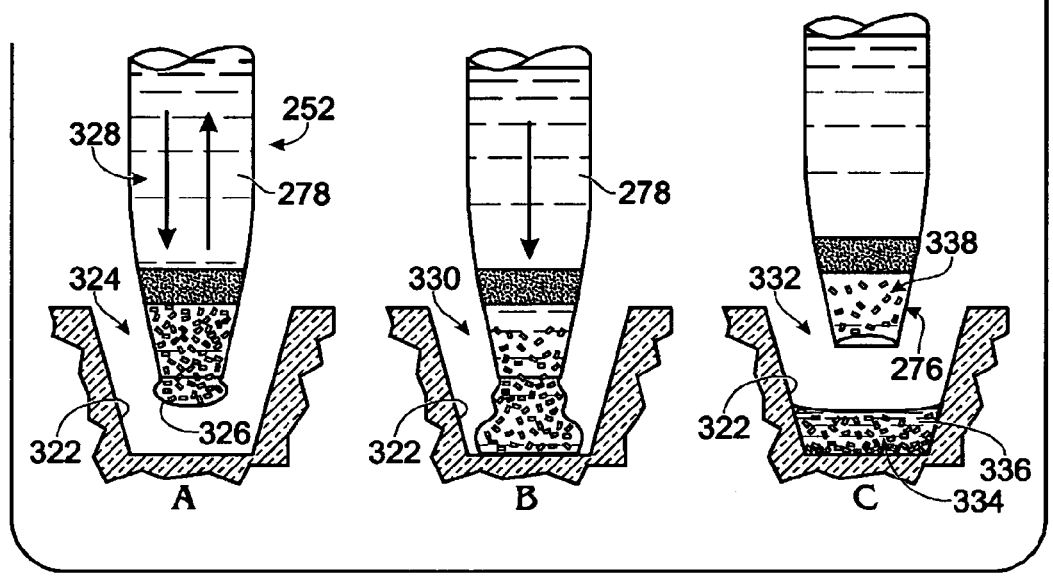
FIG. 19 is a series of fragmentary, partially sectional views of the dispenser of FIGS. 13-18 dispensing (as illustrated from left to right) a portion of its loaded particles to a well of a microplate, in accordance with aspects of the present teachings.

FIG. 19 shows a series of views, A-C, illustrating exemplary configurations that may be produced during and/or after release of particles from dispenser 252. Dispenser 252 may be disposed above and in alignment with a vessel, such as a microplate well 322. To reach this position, the dispenser, and its loaded particles may be moved from the supply site at which particles were loaded (see FIGS. 13-18) to the microplate well and/or the microplate well may be moved to the dispenser.

Panel A of FIG. 19 shows a particle configuration 324 that may be produced by outward flow of dispenser fluid 278. This flow may be induced at any suitable time after the tip portion separates from the vessel fluid (see FIG. 18), for example, as the tip portion is traveling to the microplate well and/or when the tip portion is disposed above the microplate well. The volume of the outward flow may be insufficient to create a drop that separates from the tip portion by itself, but sufficient to form a slight protrusion of fluid and/or a pendant drop 326. In some examples, the flow may include an inward flow and an outward flow induced alternately, shown at 328, performed one or more cycles. In some examples, the volume of outward flow may be greater than the volume of inward flow, to form a pendant drop 326 of increasing size with each cycle. In exemplary embodiments, for illustration purposes only, alternating flow may include, in order, about 1 μL inflow and about 2 μL outflow, performed once, twice, thrice, or more. Fluid flow, and particularly alternating outflow and inflow, may operate to loosen loaded particles so that they can be released more effectively.

Panel B of FIG. 19 shows a particle configuration 330 that may be produced by contact between dispenser fluid 278 and microplate well 322 (and/or fluid therein) and/or by additional fluid outflow from the tip portion. Contact may be induced by moving the tip portion downward (and thus closer to the microplate well), and/or by sufficient outward flow so that fluid separates from the tip portion and falls into the microplate well. In some examples, each well already may include fluid before particles are dispensed into the well. In exemplary embodiments, each well may be pre-filled with about 60 to 100 μL of fluid.

In some cases, particles may exit the tip portion but may remain associated with the tip portion. For example, the particles may be collected by surface tension within an associated pendant drip. Upon contact of the pendant drop with a receiver structure (such as a microplate well) and/or fluid therein, the surface of the pendant drop may be restructured such that particles flow/fall out of the pendant drop and into the receiver structure without passing through the surface of the drop.

Panel C of FIG. 19 shows a particle configuration 332 that may be produced after release of a portion of the loaded particles from the tip portion. In the present configuration, dispensed particles 334 and dispensed fluid 336 have separated from the tip portion. Separation may occur and/or may be facilitated by the action of gravity, surface tension, and/or separating upward movement of the tip portion away from the microplate well. However, remaining particles 338 may remain in particle space 276 (and/or exterior to the tip portion) after the first release of particles from the tip portion. Accordingly, the release processes described above and/or illustrated by panels A, B, and/or C may be repeated one or more additional times to release more of the remaining particles 338, so that a majority and/or all of the loaded particles are released to the microplate well.

The dispenser then may repeat the loading and release operation to successively dispense aliquots of particles for the particle supply. In some examples, the tip portion may be returned to the same horizontal position for reloading. Alternatively, the tip portion may be returned to an offset horizontal position. The offset horizontal position may be selected randomly or systematically, for example positions disposed in a grid or radically from a "home" position. Successive offsets may differ by any suitable or desired amount from an initial horizontal loading position, such as less than about 10 millimeters, less than about 5 millimeters, or less than about 2 millimeters, among others. Successive loading operations may adjust the vertical position to place the tip position suitably close to a remaining portion of the pile of particles. The vertical position may be selected based on a calculated and/or a sensed position of an upper surface (generally the top surface) of the pile of the particles.

Example 3

An Exemplary Dispensing System

This example describes an exemplary system 360 for dispensing particles from a supply site to a plurality of receiving sites; see FIGS. 20-27.

Figure 20:
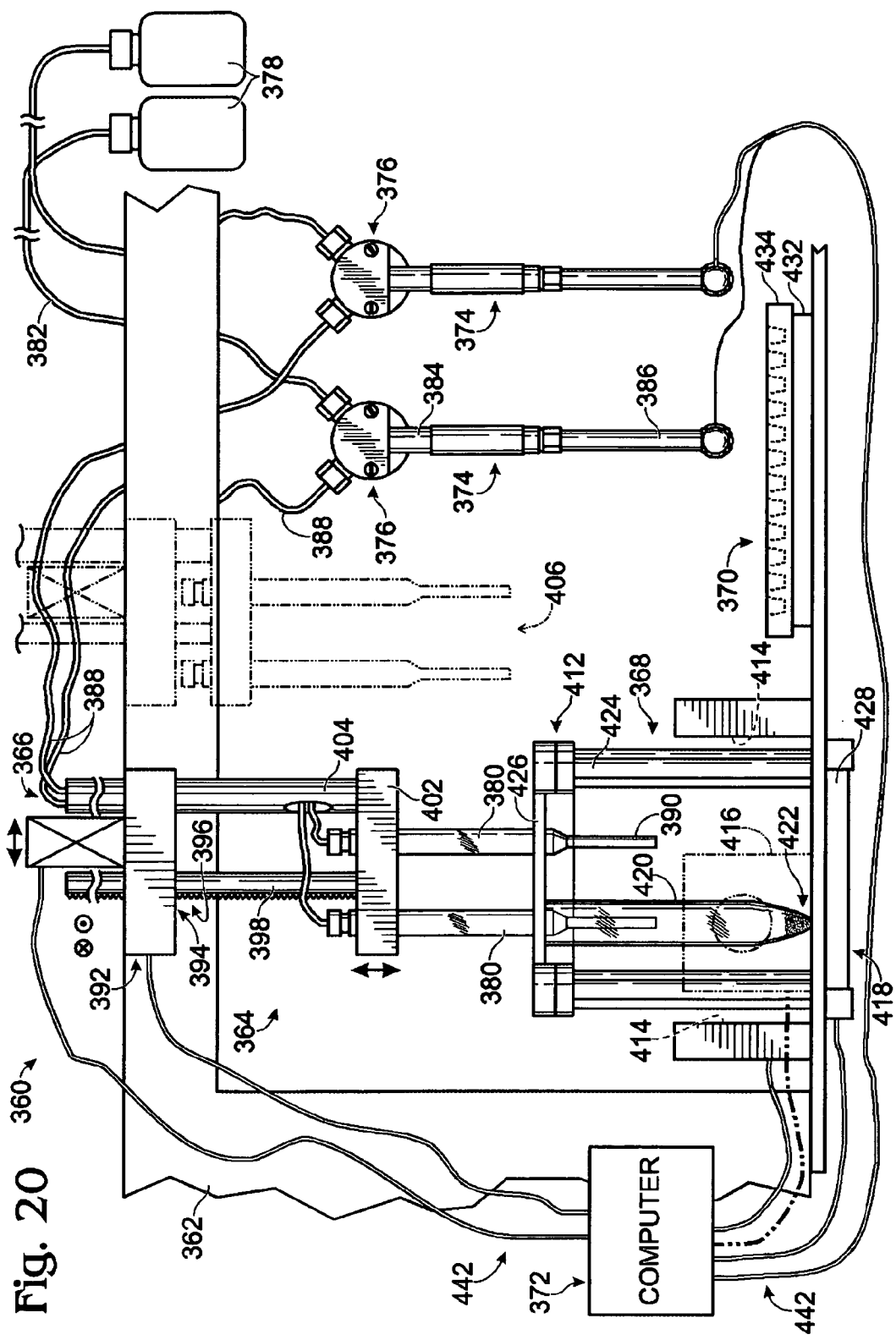
FIG. 20 is a front view of an example of a system for dispensing particles from a particle supply reservoir to microplate wells, in accordance with aspects of the present teachings.
Figure 21:
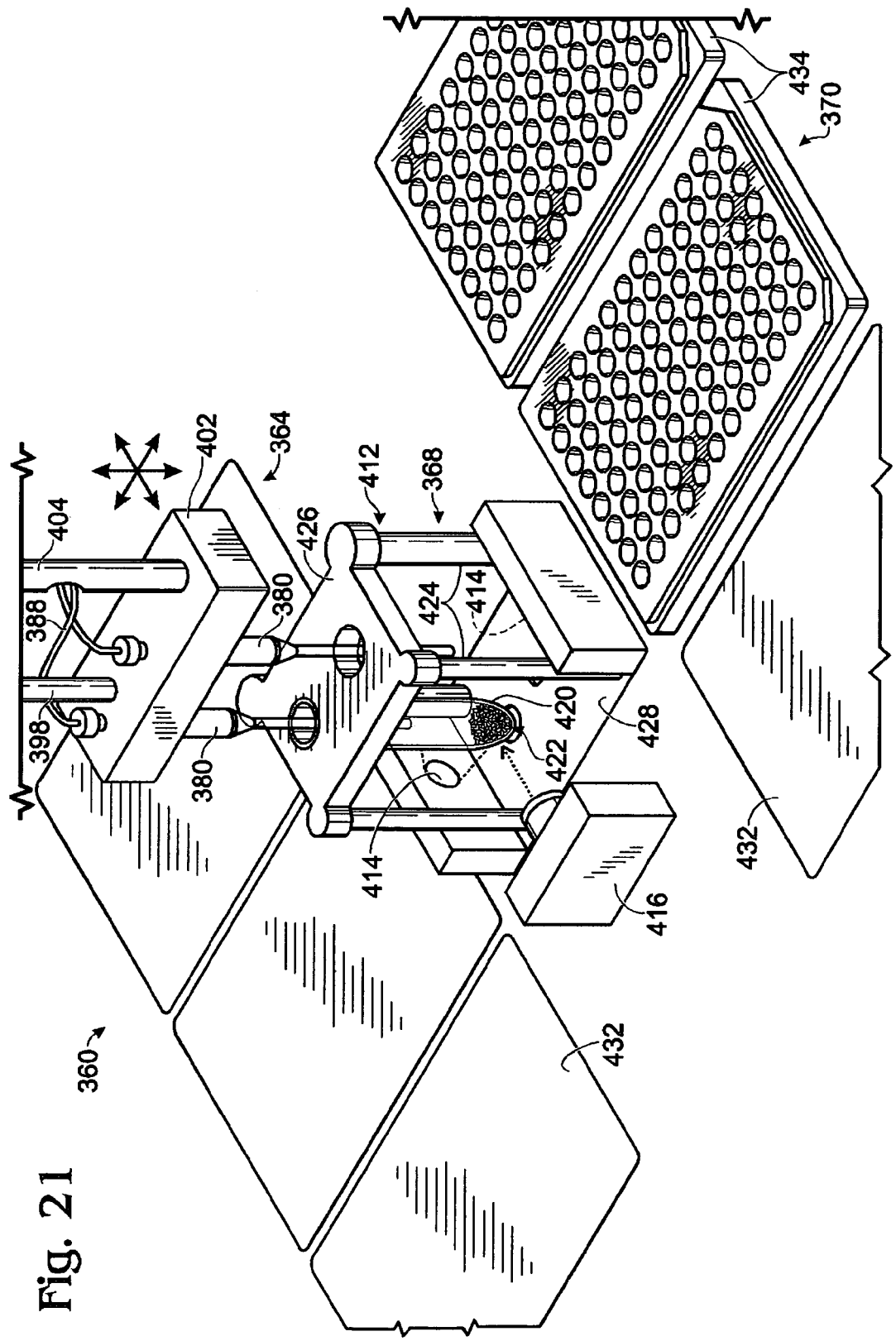
FIG. 21 is another view of selected portions of the system of FIG. 20.

FIGS. 20 and 21 show views of selected portions of system 360. System 360 may include a frame 362, a fluid transfer mechanism 364, a positioner 366, a particle loading station 368, a particle release station 370, and/or a computer 372, among others.

Frame 362 may be any structure that supports, holds, and/or protects some or all of the other structures of the system. For example, the frame may provide attachment sites for other components of the system and/or an enclosed and/or protected environment for dispensing.

Fluid transfer mechanism 364 may include one or more syringe pumps 374, valves 376, fluid reservoirs 378, and/or pipets 380, among others. In some examples, the fluid transfer mechanism may include a plurality of pipets that operate in parallel and/or in series. The pipets may load particles from the same or different particle supplies. The components of the fluid transfer mechanism may be connected in fluid communication via conduits, such as tubing 382. In the present illustration, system 360 includes a plurality of fluid transfer mechanisms, each having its own pump, valve, fluid reservoir, and pipet, and configured to be operated independently of the other fluid transfer mechanism(s).

The fluid transfer mechanism may be configured to be primed with fluid by any suitable sequence of operations. In some cases, fluid may be placed in the pipet 380 and pump 374 with an air cushion disposed there between. An exemplary sequence of operations for priming the fluid transfer mechanism to form the air cushion is outlined here. The valve 376 may be adjusted so that pump 374 is in fluid communication with a fluid reservoir 378 or a pipet 380. Accordingly, the pump 374 may draw fluid into an adjacent barrel 384 from a fluid reservoir 378 by appropriate movement of piston 386. After switching valve 376, fluid from barrel 384 may be pushed toward a pipet 380 by action of the pump. The volume defined by intermediate tubing 388 and pipet 380 may be greater than the volume of fluid pushed from the pump. The tip portion 390 of the pipet thus may be filled with air. This tip portion may be placed into a fluid supply, and then the pump actuated to draw some fluid from this fluid supply into the tip portion 390, thereby forming the air cushion within the pipet 380 and/or tubing 388. The air cushion may be configured to space fluid in the pump from the fluid in the tip portion, for example, to prevent contamination of a sterile fluid (in the pipet) with a nonsterile fluid in the fluid reservoir 378 and/or the pump 374.

Positioner 366 may include a horizontal positioning mechanism 392 and a vertical positioning mechanism 394. The horizontal positioning mechanism may be configured to move pipets 380 along a single axis or along orthogonal horizontal axes, among others. The vertical positioning mechanism may be configured to provide vertical movement of pipets 380. The vertical positioning mechanism may include, for example, a rack-and-pinion mechanism 396 to create vertical motion of rod 398 and its connected cross beam 402. Cross beam 402 may hold downwardly extending pipets 380 and an upwardly extending tube 404 (which may be hollow). Tube 404 may stabilize and/or guide vertical movement of rod 398 and cross beam 402 and/or may direct tubing 388 through the positioning mechanism and out a distal opening of tube 404 for connection to the proximal ends of pipets 380. Horizontal and vertical movement of rod 398, cross beam 402, and pipets 380 to another position within the system is represented in phantom outline at 406. Portions of a dispenser that may be suitable in system 360, particularly the fluid transfer mechanism and/or selected aspects of the positioner mechanism, may be provided by a Cavro MSP 9250 "mini sample processor," available commercially from Tecan Systems, Inc.

Particle loading station 368 may include a vessel stand 412, one or more lights 414, a camera 416, and/or a position sensor 418, among others. Further aspects of the position sensor are described below in relation to FIGS. 24-27.

Vessel stand 412 may be configured to support one or more vessels 420 holding particles 422 to be loaded and dispensed. The vessel stand may include any suitable support structure, such as one or more legs 424 (or walls) and a receiver structure 426 configured to receive the vessels. In the present illustration, receiver structure defines a plurality of openings sized to receive vessels 420 and restrict their lateral movement. Vessel stand 412 also may include a floor 428. The bottom of vessel 420 may be supported by the floor and/or by a portion of a position sensor coupled to the floor, among others.

Lights 414 and camera 416 may be configured, respectively, to illuminate and image the particle loading station. Accordingly, lights 414 (or a single light) may be disposed in any suitable location, such as adjacent a lower region of vessel(s) 420. Any suitable light sources may be used, including one or more light-emitting diodes (LEDs), an arc lamp, a fluorescent lamp, and/or an incandescent lamp, among others. Camera 416 may be disposed for imaging the particle supply site and particularly a region of vessel(s) 420. Images obtained by the camera may be sent to a display for viewing by a user of the system. The camera and display thus may function as a magnifier, for example, to aid a user monitoring aspects of the dispensing process and/or to increase the accuracy with which a user may position the dispenser tip relative to the particles before and/or during dispensing, among others. Alternatively, or in addition, the images may be analyzed by a processor to determine information about the particles and/or the dispenser tip, such as their relative positions, the status/efficiency of particle loading, and/or the number/volume of particles in the vessel, among others. Camera 416 may be configured to collect digital and/or analog images.

Particle release station 370 may include support structures for one or more receiving vessels. In the present illustration, particle release station includes receivers 432 for a plurality of samples holders, such as microplates 434. Each receiver may be configured to position and/or retain a microplate, for example, with clips, pins, clamps, etc. The receivers may position wells of the microplates reproducibly and thus in a predefined manner, so that computer 372 may receive position data for the wells and re-use this same position data for a succession of microplates placed in each receiver.

The computer 372 may be configured to control dispensing automatically. Accordingly, the computer may be in communication with positioner 366, pumps 374, valves 376, lights 414, camera 416, position sensor 418, a display, and/or a user interface (such as a keyboard, touch screen, keypad, etc.), among others, to receive signals from, and/or to send signals to, these devices. Communication may be with wires 442, as shown in the present illustration, and/or may be wireless.

Figure 22:
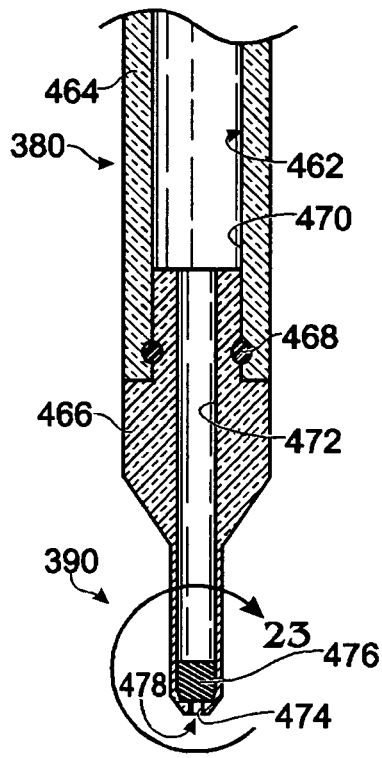
FIG. 22 is a fragmentary, sectional view of a dispenser tip and its associated barrel from the system of FIG. 20.
Figure 23:
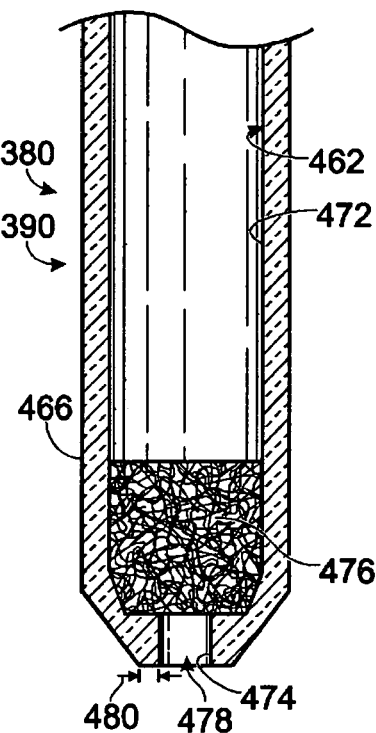
FIG. 23 is a fragmentary, sectional view of the dispenser tip and barrel of FIG. 22, taken generally from the region indicated at "23" in FIG. 22.

FIGS. 22 and 23 show a distal portion of one of the pipets 380, particularly dispenser tip 390. The barrel of pipet 380 may define a conduit 462 with a single component or a plurality of components, such as upper and lower components 464, 466. These components may be fitted together to form a fluid-tight seal, and thus may include a gasket 468 at an interface of the components to resist leakage. Conduit 462 may narrow as it extends to tip 390, either stepwise or gradually. In the present illustration, conduit 462 decreases stepwise from a wide bore 470, to an intermediate bore 472, and then to a distal narrow bore 474. Narrow bore 474 may be tapered or nontapered. In some examples, the narrow bore may flare outward towards the end of the tip, for example, with a slope of about two to four degrees. A filter 476 may be disposed in the intermediate bore 472, adjacent the narrow bore, to define, with narrow bore 474, a particle loading space 478. The filter may formed of any suitable material that creates a pore size smaller than the particles, including fibers, sintered granules, an etched matrix, etc.

Tip 390 may have any suitable shape. For example, the tip may have a rounded or angular exterior. In the present illustration, the tip has a distal width, shown at 480 in FIG. 23, measured along a surface extending substantially orthogonal to the central axis of the pipet. The width of this surface may be sufficient to create a Venturi effect when fluid is drawn generally horizontally between the surface and the particles. In some examples, the width may be at least about one-fourth the diameter of the particle loading space. The distal opening of the tip may have any suitable geometry and size. In some examples, the ratio of the diameter of the distal opening to the distance from the opening to the filter above this opening may be at least about 1:2. In some examples, the internal diameter of the tip may taper (decrease) along the tip from the opening to the filter, so that the internal bore of the tip flares outward as it extends from the filter to the distal end opening of the tip. An exemplary flare may be about three degrees. This flare may facilitate release of an injection molded tip from its mold, and/or may create a flow velocity gradient in the tip below the filter, with an increased rate of fluid flow closer to the filter.

Figure 24:
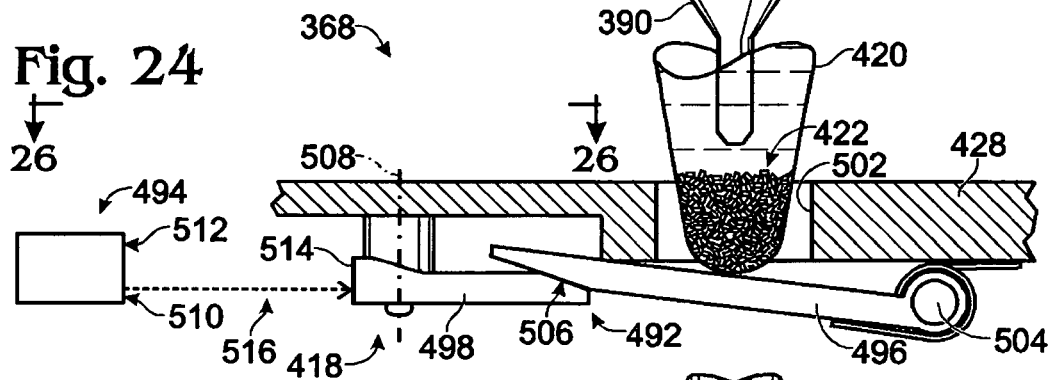
FIG. 24 is a partially sectional view of a position sensor included in the system of FIG. 20, with the particle reservoir in a nondeflected configuration.
Figure 25:
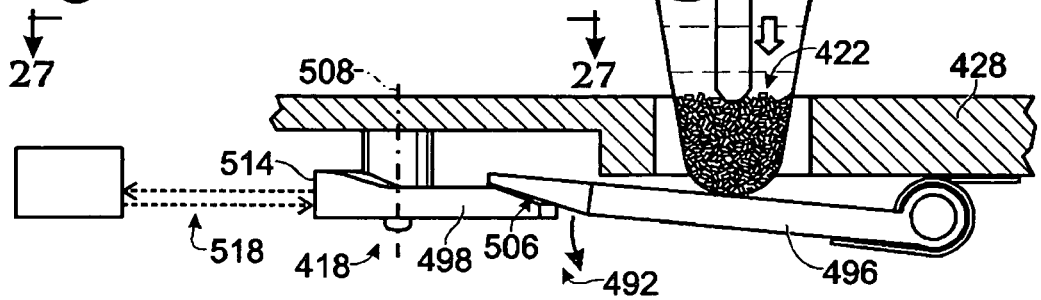
FIG. 25 is another partially sectional view of the position sensor of FIG. 24, with the particle reservoir in a deflected configuration.
Figure 26:
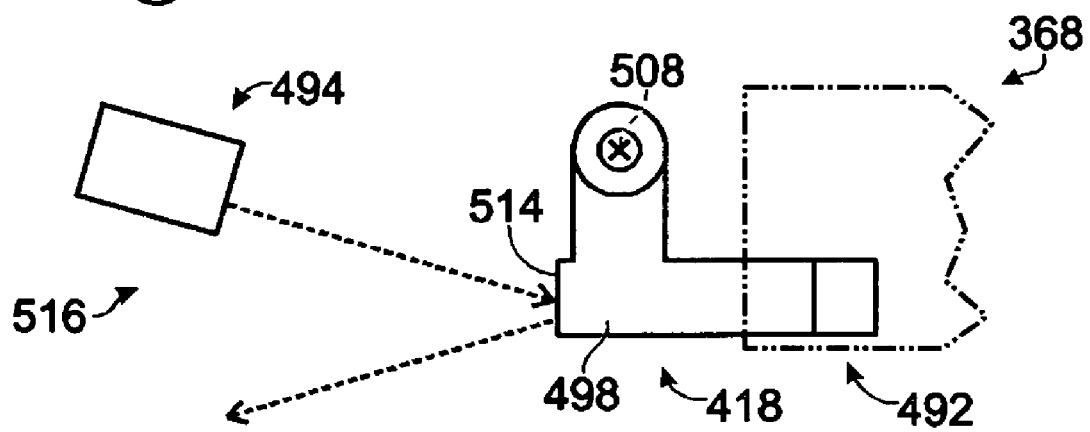
FIG. 26 is a top view of selected portions of the position sensor of FIG. 24, with the particle reservoir in the nondeflected configuration.
Figure 27:
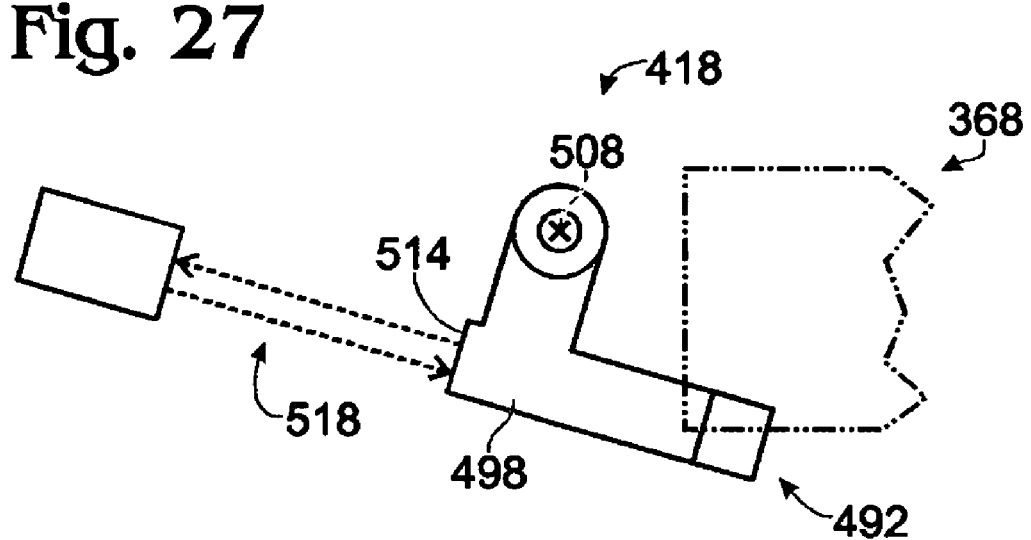
FIG. 27 is a top view of selected portions of the position sensor of FIG. 25, with the particle reservoir in the deflected configuration.

FIGS. 24-27 show various views of position sensor 418 of particle loading station 368. FIGS. 24 and 26 show corresponding side and top views, respectively, of the position sensor in a non-actuated (off) configuration. FIGS. 25 and 27 show corresponding side and top views, respectively, of the position sensor in an actuated (on) configuration caused by downward movement of the particles by the dispenser tip. In alternative embodiments, the position sensor may be configured to sense a plurality of vessel/particle positions.

Position sensor 418 may include a switch assembly 492 and a detector mechanism 494.

The switch assembly may include first and second switch members 496, 498, respectively. First switch member 496 may be positioned below an opening 502 formed in floor 428 of the supply station 368 and may be configured to contact and support vessel 420. The first switch member may be movable relative to a vertical axis, for example, hinged to pivot about a pivot axis 504 and/or slidable translationally. The first switch member also may be biased toward a nondeflected configuration, so that this switch member may be deflected downward by application of a force, and then may move upward again after removal of the force. The second switch member also may be biased toward the nondeflected configuration.

Movement of first switch member 496 may be coupled to movement of second switch member 498. For example, in the present illustration, the switch members engage one another along beveled surfaces 506, so that pivotal movement of the first switch member about pivot axis 504 induces pivotal movement of second switch member about an orthogonal pivot axis 508.

Detector mechanism 494 may include an emitter 510 and a detector 512. The emitter may emit a signal, such as electromagnetic radiation (for example, infrared radiation) or sound. The detector may be configured to sense the emitted signal when it is directed back to the detector by a reflector 514 disposed on the switch assembly.

FIGS. 24 and 26 show switch assembly 492 in an off configuration. First switch member has not pivoted sufficiently from its resting position. Accordingly, reflector 514 does not reflect the emitted signal back to the detector, shown at 516.

FIGS. 25 and 27 show switch assembly 492 in an on configuration. First switch member has pivoted downward from its resting position due to a force exerted on the particles and vessel 420 by the dispenser tip 390 moving downward into contact with the particles. Accordingly, reflector 514 reflects the emitted signal back to the detector, shown at 518. With each loading operation, position sensor 418 may send data to computer 372 that indicates if and when the switch assembly was actuated and/or de-actuated, so that the computer may adjust the vertical position of the dispenser tip during the present or successive loading operations. For example, if the switch assembly was never actuated by sufficient deflection, the tip dispenser may be lowered an added distance (or with larger or more increments) on subsequent loading operations. Alternatively, if the switch assembly was actuated sooner and/or longer than expected, the tip dispenser may be lowered less (or with smaller or fewer increments) on subsequent loading operations. These adjustments in vertical positioning determined by the position sensor may be used alone or in combination with vertical adjustments based on calculated vertical positions of the particle supply.

Example 4

An Exemplary Dispersion Apparatus

Figure 28:
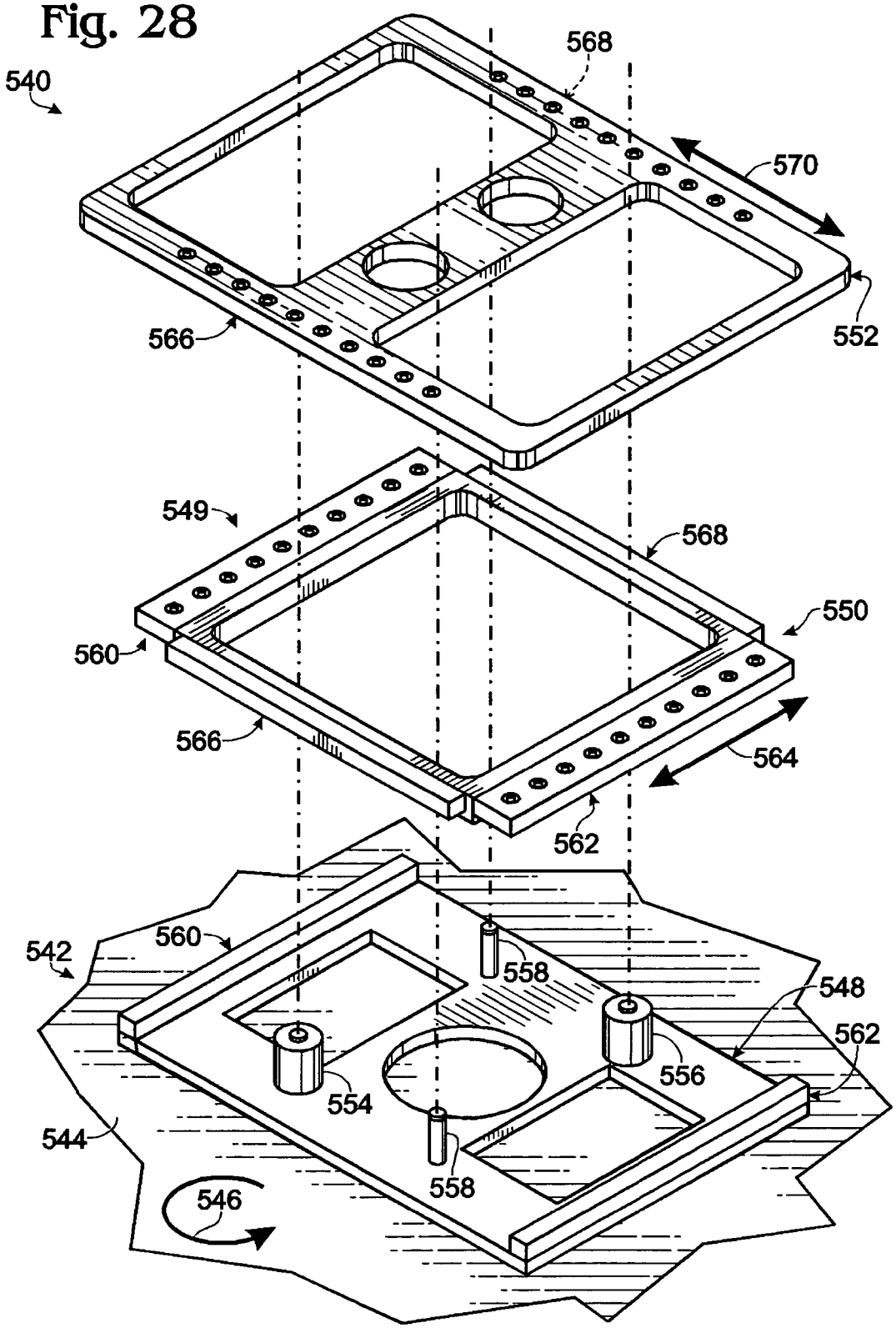
FIG. 28 is an exploded view of selected portions of an example of an apparatus for particle dispersion with the apparatus secured to an orbital shaker, in accordance with aspects of the present teachings.
Figure 29:
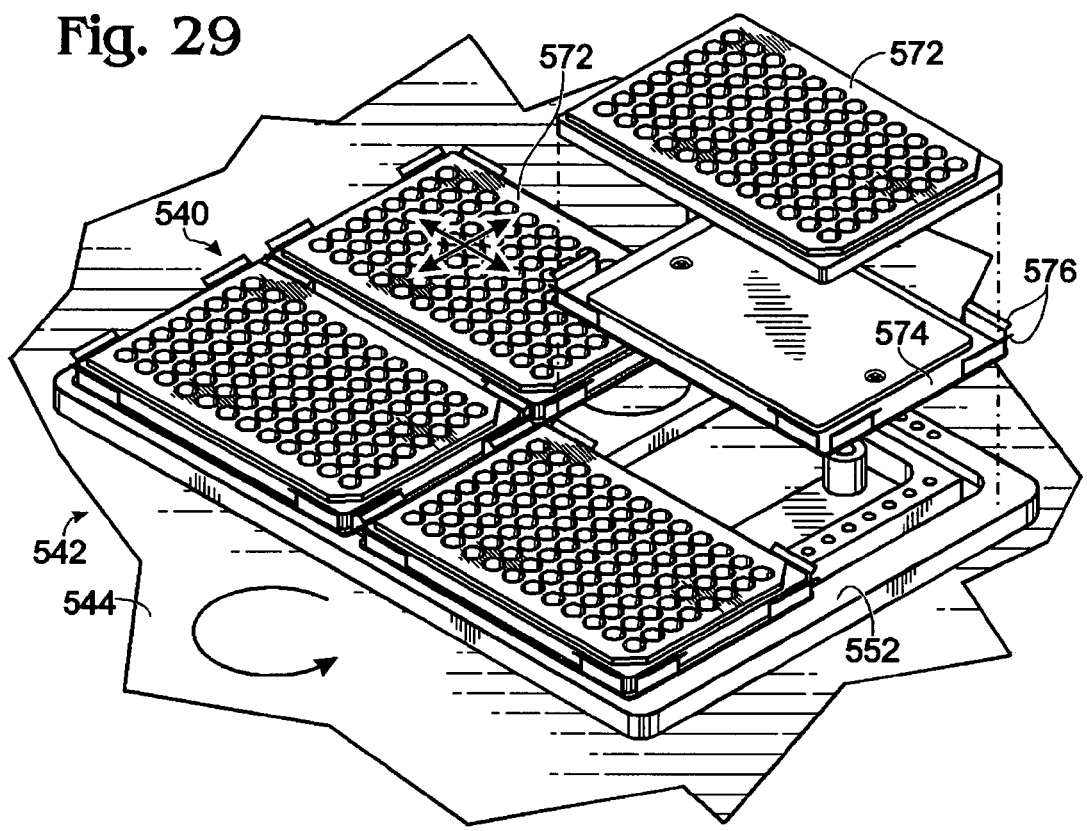
FIG. 29 is another view of the apparatus of FIG. 28 in a mostly assembled configuration and holding microplates.
Figure 30:
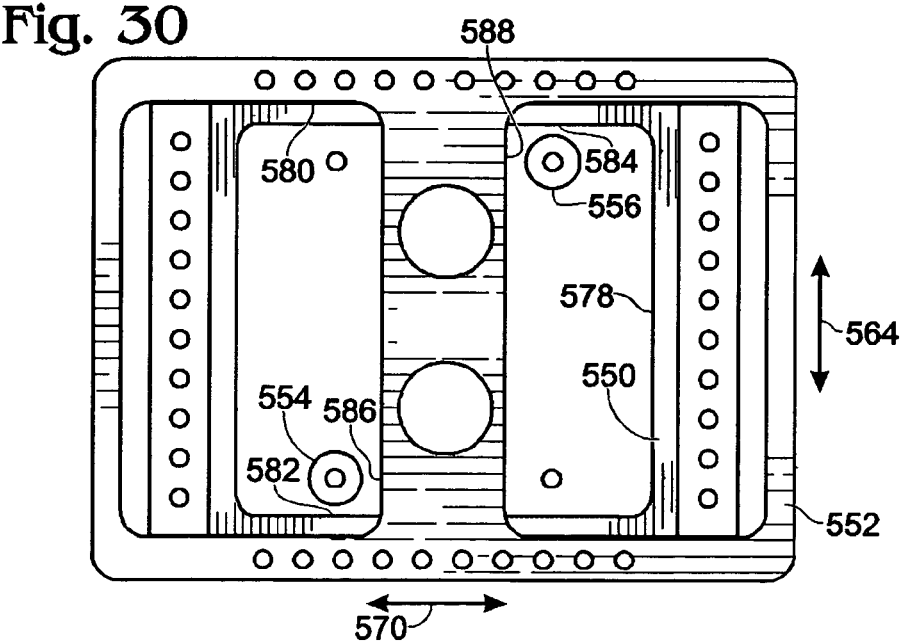
FIG. 30 is a top view of the selected portions of the apparatus of FIG. 28 in an assembled configuration.

This example describes an exemplary dispersion apparatus for dispersion of particles; see FIGS. 28-30.

FIG. 28 shows an exploded view of selected portions of an exemplary apparatus 540 for particle dispersion secured to an orbital shaker 542, particularly an orbiting platform 544 thereof. Orbital shaker 542 may be configured to have any suitable orbital motion, shown at 546. In exemplary embodiments, for the purposes of illustration, the orbital shaker may have an orbit diameter of about 5-30 millimeters. Furthermore, the orbital shaker may be configured to orbit at any suitable rate. In exemplary embodiments, for the purposes of illustration, the orbital shaker may have a maximum orbital rate of about 100-1000 revolutions per minute.

Apparatus 540 may include a base 548 and a guide mechanism 549 coupling the base member to a vessel holder. The guide mechanism may be configured to convert orbital motion of the base member into non-orbital motion of the vessel holder. In some embodiments, the guide mechanism may convert the orbital motion into interrupted linear motion along two or more linear segments. The guide mechanism may include a lower member 550 and an upper member 552 that are slidably connected to each other and to the base. Each of these members may have any suitable shape and size. In some examples, each of the members may be formed as a generally planar structure, such as a plate.

Base 548 may be secured to platform 544, such as with clips, clamps, threaded fasteners (screws, bolts, and/or nuts, among others). The base may include one or more bumpers (stops) 554, 556 that operate in the guide mechanism to restrict sliding motion of the lower and upper members 550, 552. In some examples, the bumpers may be placed on posts 558 of the base.

Lower member 550 may be slidably connected to base 548 with one or more lower guide assemblies 560, 562. Here, lower guide assemblies 560, 562 are disposed on opposing sides of the base and the lower member. Each lower guide assembly may guide non-orbital motion of the lower member, generally linear motion, shown at 564, of the lower member relative to the base.

Upper member 552 may be slidably connected to lower member 550 with one or more upper guide assemblies 566, 568. Each upper guide assembly also may be configured to guide non-orbital motion, such as generally linear motion, shown at 570, of the upper member relative to the lower member. The first and second linear motions 564, 570 may be at transverse to each other, for example, generally orthogonal to one another. The lower and/or upper guide assemblies may include bearings or other mechanisms that assist sliding motion.

FIG. 29 shows apparatus 540 in a mostly assembled configuration and holding microplates 572. Dispersion apparatus 540 may be configured to hold any suitable number of microplates. In the present illustration, upper member 552 may be secured to four microplate holders 574. Each holder 574 may include clips 576 or other retention structure to hold the microplates in position on the dispersion apparatus during dispersion.

FIG. 30 shows a top view of the dispersion apparatus 540 in the absence of microplates and their holders. Stops 554, 556 may be positioned to restrict linear motion of the lower member 550 and upper member 552 by contact with regions of the lower and upper members. The stops may extend into openings 578, 580 defined by the lower and upper members, respectively, so that collision of stops 554, 556 with walls of the openings defines the length of the linear paths along which the plate members can slide. For example, first stop 554 may restrict linear motion of lower member 550 parallel to motion axis 564 by contact with wall region 582, and second stop 556 may restrict linear motion of lower member 550 parallel to motion axis 564 in the opposite direction by contact with wall region 584. Thus, the spacing of stops 554, 556 from corresponding wall regions of the plate members 550, 552 may determine the distance of travel parallel to motion axis 564. Similarly, the distance of linear motion parallel to motion axis 570 may be determined by the spacing of stops 554, 556 from corresponding wall regions 586, 588 of upper member 552.

Example 5

Exemplary Pipet and Loading Configurations

This example describes exemplary pipet configurations, fluid flow rates, and tip positions during carrier loading.

Tests were performed to optimize pipet performance. Initial attempts at fluid-mediated dispensing of glass carriers (particles for carrying cells) involved drawing up a controlled number of carriers into pipets of various bore sizes. Even using a Cavro MSP-9000-series dispenser (where the z-axis can be set to one-hundred micron accuracy, and the syringe to less than one microliter volumes), the results were not satisfactory. In particular, the number of carriers dispensed was too low and too variable.

Tests were performed to optimize the tip of the pipet. The tip was modified to include an inverted cup at the end of the tip. The sides of the cup were defined by the walls of the pipet and the base of the cup (the top of the inverted cup) by a filter or frit disposed in the bore of the tip and spaced suitably from the end of the tip. Frit materials of various types were used to form the cup. Each cup was tested for it ability to retain carriers in the cup while fluid flowed through the cup, past the frit, and into the body of the pipet tip.

The dimensions of the cup may be one of at least two characteristics that control the number of carriers picked up from a stack of carriers in a flask. Given sufficient flow rate of the fluid in which carriers are disposed, a desired configuration of the cup may involve a trade-off between keeping the cup depth "shallow" and sufficiently narrow, such that the flow of fluid is equally distributed across the cup and the fluid (surface tension) across the mouth of the cup is stabilized. In particular, if the height of the cup is too great, a clog may form before the carriers fill the top of the cup. Formation of a clog with carriers may lead to less than expected numbers of carriers loaded into the cup, along with an increase in the variability of loading (for example, due to clogs forming sporadically and at unpredictable heights). A cup that is too wide may be difficult to configure so that the cup produces few or no eddies or dead spaces as fluid is flowing through it. Also, a large opening at the mouth of the cup may reduce the stability of a pendant drop of fluid formed there. As a result, fluid and carriers may leak out of the tip after it is loaded with carriers.

Suitable tips for dispensing carriers and other particles may be polypropylene tips with a tip orifice diameter of about 1.6 to 2.3 mm. The particular diameter selected may be based at least partially on the size of particles to be dispensed. The walls of the tips, defining the orifice in the cup, may be cylindrical (that is, vertical) or may slope inwardly (or outwardly) to the frit, to produce, for example, a generally frustoconical compartment inside the cup. In some examples, the cup may slope inwardly with a slope of about three degrees from vertical to the top of the cup. In some examples, the cup may have a height of about 1.4 mm [~outside diameter−(2*(tan(3degrees)*1.4 mm))]. Note that at these dimensions, the size of exemplary carriers (500 microns×300-500 microns× 70-100 microns) may be a significant fraction of the dimensions of the cup. Therefore, small changes in the dimensions of the cup may not be reflected in a proportional change in the carrier capacity of the tip. In contrast, carriers that are much smaller than the cup, such as beads of less than five microns in diameter, may not show this nonlinear dependence on cup dimensions. In this regard, tips with an orifice diameter of 1.5 millimeters or less may exhibit a poor ability to pick up the exemplary carriers described above. On the other hand, tips with orifice diameters of greater than about 2.3 mm also may be inefficient with these exemplary carriers. In particular, the tip may be too wide for the surface tension at the end of the tip to reliably retain the carriers in the tip as the tip separates from the fluid in the flask.

The rate of fluid flow during carrier loading into the cup of a pipet tip also may be important. In particular, with a selected configuration of carriers and pipet tip, a threshold rate of fluid flow may be necessary to completely fill the cup of the pipet tip with carriers. For example, with the exemplary carrier and tip dimensions described above, a threshold flow rate of about nine mm/second (linear flow rate through the tip) may be necessary to fill the cup with carriers. With decreasing flow rates below this threshold, a decreasing percentage of the tip may be filled with carriers. With a flow rate of about six mm/sec or less, carrier pickup may be essentially zero. These observations may be dependent on the flow rate through the pipet tip also being comparable at the surface of a stack of carriers from which loading is performed. Since the flow rate may fall off with increasing distance from the pipet tip, the tip should be relatively close to the stack of carriers during loading. Generally, the pipet tip may be within about one mm of the carriers as the carriers are drawn into the cup of the pipet tip. In some examples, the tip may be placed less than about 200 microns from the carrier stack as the carriers are loaded.

Example 6

Exemplary Tip Positioning and Flow Adjustments

This example describes exemplary aspects of dynamic tip positioning and flow adjustment during carrier loading.

At least two steps may be involved in placing a pipet tip in very close proximity to a stack of carriers. A first step may calculate the current, theoretical height of the stack, and a second step may position the tip such that differences between the theoretical height and the actual height are negated. Alternatively, or in addition, the current height of the stack may be measured or sensed, as described elsewhere in the present teachings.

The theoretical height of the stack at any time may be calculated based on the initial height of the carrier stack (or a known height at any time during dispensing), the internal geometry of the flask holding the stack, and the volume of carriers loaded into the tip during each loading operation. At the start of a dispensing series, the initial height of the carrier stack in the flask may be inputted by a user or determined automatically. For a particular tip size, the average number of carriers loaded in a loading operation may be determined empirically. From the known geometry of the flask and the initial height of the carriers, the volume of the dispensing flask (and therefore the effective volume of the carriers) at that height may be calculated. Finally, from an empirically determined average packing ratio of the carriers (carriers per microliter), the initial number of carriers in the dispensing flask may be calculated/estimated.

At any point in the dispensing series, the fractional number of carriers remaining in the dispensing flask may be a proxy for the fractional remaining volume occupied by the remaining carriers.

It then follows that at each loading operation, this remaining fractional volume may be related to the remaining fractional height of the carrier stack (that is, a ratio of the new height of the stack of carriers relative to the initial height of the carriers in the dispensing flask). For a frustoconical flask, the relationship is $(Ht_{new}/Ht_{init})=(Vol_{new}/Vol_{init})^{(1/3)}$, that is, the cube-root of the remaining fractional volume is equal to the remaining fractional height. For a cylindrical flask, the remaining fraction volume may be directly proportional to the remaining fractional height. Thus, the theoretical new height of the carriers in the dispensing flask may be calculated.

This theoretical height however may deviate from the real new height in part because of the angle of repose of the carriers. With any significant angle of repose, the stack of carriers may not behave as a fluid, and as a result, the height of the carriers at the very center of the stack of carriers actually may be lower than the height calculated above, while the height of the carriers at the perimeter of the stack may be higher than the calculated height. Another possible deviation may arise due to differences in the packing ratio of the particles with position in the stack and/or by settling of the particles that arises from agitations during prior dispensing cycles.

It may be important to resolve the difference in theoretical from actual height so as to place the tip in close proximity to the carriers. One approach may involve, either via calculation or empirical finding, determining the maximum deviation from theoretical, and then gently lowering the tip that amount, plus a little more, such that the tip is expected to be within the stack of carriers. During this "supplemental" positioning of the tip into the carriers, it may be important to have a sufficient yet gentle outflow of fluid, termed a "fluff," from the tip to facilitate fluidizing (suspending) carriers immediately under and adjacent the tip. An insufficient fluff flow rate may result in crushing or otherwise damaging carriers under the tip (or the tip itself) as the tip descends. However, this flow rate may be low enough to minimize detachment of cells from their carriers. Fortunately, an outflow rate sufficient to fluidize carriers out of the way of the tip may be considerably lower (seven mm/sec) than that required to draw carriers into the tip, so cell detachment may be avoided during the fluff.

The downward movement of the tip (z-axis) into the carrier stack during the fluff may be coordinated with the fluff flow rate. If the tip descends too fast, there may be insufficient time for the fluff to move carriers out of the way of the tip. It also may be desirable to terminate the fluff just prior to the end of downward movement of the tip. This time of termination may allow the tip to move into an area last voided of carriers by the fluff, thereby leaving the tip in very close proximity to the carriers beneath the tip. Terminating the fluid flow of the fluff too early may result in the descending tip crunching into the carriers left in the path of the tip. Terminating the fluid flow too late may space the tip too far from the carriers. The use of a "spring-loaded rack to hold the supply vessel may significantly reduce the likelihood of crunching the carriers.

An alternate approach to resolving the theoretical and actual top of the carriers may be to include in the calculation an approximation of the depth of the recess at the top surface of the carrier stack caused by the angle of repose. This recess or "dimple" may grow until the depth of the dimple, divided by the tangent of the angle of repose (~34° for the exemplary carriers of Example 5), is greater than the radius at the top of the stack of carriers. That is, as the dimple becomes deeper, there may not be enough lateral distance to the wall to keep the slant of the carriers at or below the angle of repose. As the dimple becomes too deep, a sufficient number of carriers may fall from the surrounding region into the dimple until the depth-to-radius ratio of the dimple again supports the angle of repose.

In practice, the actual height of a carrier stack may deviate quickly from the calculated height during removal of the first 10-15 loads of carriers when using exemplary tips and flasks. From that point on, the difference between the two heights may remain constant until the bottom of the flask is approached. At that time, the change in actual height with each deposition may be less than the change in the calculated height, such that the two heights converge and become equal as the flask becomes depleted of carriers, or when it is no longer possible for the tip to withdraw any more carriers.

Once the tip is appropriately placed, carriers may be drawn up into the cup of the tip. With exemplary glass carriers, the fluid draw rate may need to be selected appropriately. In particular, the flow rate may be high enough to levitate the carriers from the stack into the cup, yet gentle enough to retain sufficient cells on the carriers for subsequent assays. This balance also may include the time during which the draw flow rate is active and may vary with different cell types/lines depending on their adherence characteristics. Since there may be no carriers in the cup at the start of the draw (no obstruction to fluid flow), and since the tip may be placed in very close proximity to the carriers, a slightly slower draw speed may be employed to pick up the first carriers (60-95% of max draw speed). This slower draw speed may produce a partially filled cup. Note that the carriers now present in the cup may partially obstruct any subsequent flow through the cup. Also, because carriers have been removed from the top of the stack, the tip may be farther from the carriers remaining in the flask.

Therefore, in an exemplary sequence, after 100-200 milliseconds, the tip may lowered about 400 microns (a "drawdrop" sequence) to reestablish close proximity to the carriers. In some examples, the draw fluid flow may be increased about 5-40% during and/or after the "drop." (One can think of this as lowering a vacuum cleaner hose.) The elevated flow rate may be maintained for about 100 milliseconds, at which time the fluid draw speed may be reduced, for example, by about 60%, to the "holding speed" (about 4.5 mm/sec).

If the draw-drop is too far, the descending tip may crunch the carriers. Too small of a draw-drop and the number of carriers drawn into the tip may fall off and be less consistent. Extending the time of these operations only may serve to increase the time during which cells are subjected to high flow rates. In addition, as the tip fills, there may be less free volume in the tip for flow of fluid, thereby increasing the effective flow rate to which the cells may be exposed in the tip.

Upon switching to the holding pump speed, the tip may be raised slowly to a safe distance above the top of the carriers (1-2 millimeters). Slowly raising the tip may be suitable, as moving the tip at this point at a high speed may be equivalent to rapidly removing a piston from a body of water. Accordingly, rapid movement may create a very strong turbulence, and if performed too closely to the carriers, the turbulence may be strong enough to fluidize significant numbers of carriers. As a result, cells may be damaged and/or may detach from the carriers. This turbulence can also inconsistently affect the stability of the "beard of carriers" extending below the bottom of the tip.

At this point, the tip still may be disposed in the fluid of the flask. The tip may be lifted from the fluid and transported to a well into which the carriers are to be dispensed. The holding pump speed still may be active as the tip is being raised out of the fluid in the flask. This use of the pump at this point may be suitable because as the tip rises, the hydrostatic pressure in the tip may increase.

To keep culture media (an exemplary fluid in the dispensing flask) from touching the tubing which connects the syringe pump to the dispensing tip, an air bubble may be positioned between the culture media and phosphate-buffered saline that may be used in the syringe and tubing. The use of an air bubble may reduce contamination and cleaning problems. However, this air bubble may act as an "air spring" as it is both compressible and expandable, subject to the pressures impinging upon it. As the tip is rising from the flask, the increase in the height of the culture media in the dispensing tip relative to the fluid level in the flask may increases the weight of culture media impinging upon the air bubble. As a result, the air bubble may expand slightly, and in the absence of an inward holding action of the pump, fluid may flow out of the tip.

When the tip actually exits the top of the fluid in the flask, the single surface tension layer holding the fluid in the flask and in the tip together may play a role. In particular, this layer may increase the pull on the fluid in the tip, and because of the air bubble, may generate a flow from the tip into the flask, until the tip and flask fluid bodies physically separate and reform their own surface tension boundaries (one at the top of the fluid in the flask, the other sealing the orifice of the tip.

Any resulting flow of fluid from the tip back into the flask may produce enough turbulence to cause loss of carriers from the tip, for example, greater than 80% of the carriers may fall out of the tip and back into the flask in some embodiments. The holding speed may be set at or above the bare minimum that neutralizes these reverse flows and stabilize the carriers in the tip. The time at which the tip actually exits the fluid in the flask may be determined. At or after that point, the pump speed may be set to zero. Continuing the holding pump speed beyond this point may, albeit slowly, suck air into the tip, which may be desirable to avoid.

Example 7

Exemplary Release of Loaded Particles

This example describes exemplary approaches to releasing loaded particles.

A simple outward flow of fluid may suffice to release the carriers into the well of a microtiter plate. The outward may have any suitable volume, such as about 25 to 100 microliters of fluid.

Additional release steps may be desirable to improve the release of particles. In particular, carriers (particularly glass carriers) may need to be jostled loose from the cup to improve the efficiency of their release. In particular, the hardness/sharpness of the glass carriers and the relative softness of the polypropylene tip (not that polypropylene is itself a "soft" plastic) may cause the carriers to stick the interior walls of the tip. For example, the corners of some carriers may become wedged into the inside of the cup, thereby both stabilizing the carriers in the cup, and hindering their direct release into a well. Tips have been observed to become finely, but significantly, scratched, apparently from the edges of glass carriers loaded into the tips.

At least two approaches may be used to loosen up the carriers. In a first approach, fluid contact between the fluid in the tip and the fluid in the well may be repeatedly made and broken. One or more cycles may be used, and in some examples, at least 3-4 cycles may be used. As mentioned above in regards to raising the tip out of the flask, the separation of the fluid into two separate bodies may be an energetic event. (Multiple make-and-break cycles may be suitable because, for example, the mass of the fluid in the well may be insignificant compared to that in the flask.) In some examples, this approach (lowering and raising the tip) may be successful in releasing all the carriers from the tip greater than 90% of the time. A second approach may involve quickly moving 1-2 microliters of fluid in and out of the tip. (In some examples, the capacity of the cup may be about 24 microliters.) Despite the formation of a pendant drop at the tip, the loosened carriers may be retained completely in the drop by surface tension. In and of itself, this pulsing in and out may not be efficient at releasing carriers into the well. However, combining the pulse method (for example, one pulse or 2-3 pulses) plus one-to-two cycles of touching the resulting drop to the fluid in the well may release all of the loaded carriers.

The release method described above may have other advantages. First, the pulse steps (alternating flow) may be performed much more quickly than the dip (contact) steps. Further, since the pulses may not create a drop of any significant size, it may be unnecessary to wait for the tip to be in the well before starting the pulse/stutter routine. In particular, the pulse steps may be performed while the tip is en route to the well. As a result, fewer touch steps may be necessary for efficient release of the carriers and carrier release may be quicker by reducing the number of touch operations performed.

An exemplary release protocol may include the following steps: (1) performing three inflow-outflow cycles, with each cycle including 1 uL of fluid inflow and 2 uL of fluid outflow, (2) pushing out about one-half of the 25-60 uL volume to be dispensed, (3) touching the tip or a drop at the tip to fluid in the well, (4) raising the tip, (5) expelling the other half of the total dispensed volume, and (6) touching the tip/drop to the fluid in the well again. The tip then may be returned to the dispensing flask as one dispensing operation is completed.

Example 8

Exemplary Dispersion of Particles

This example describes exemplary aspects of particle dispersion.

Dispersion may be performed to position any suitable number of carriers, such as over seventy carriers, in a microplate well so that there are minimal overlaps and unidentifiable carriers. The carriers may be tiled in a single layer in the center of the well. Geometrically, about 125 exemplary carriers (see Example 5) can be tiled in a well. However, the greater the number of a particular size of carriers deposited in a well, the greater the chance of irresolvable overlaps.

While carriers without cells may be dispersed in a microplate well by swirling the microplate, the presence of cells on the carriers may increase friction between the carriers and the microplate surface substantially. A general approach to dispersing carriers attached to cells may involve smartly striking, from various directions, a slanted microplate holding dispensed carriers.

In some approaches, the microplate may be held at an angle of about 45 degrees and sharply struck on its edge disposed at the top of the angle. The plate then may be rotated as needed and the process repeated. Good dispersion may be identified by eye by any combination of the following criteria: (1) the absence of large clear areas (devoid of carriers) in the well, (2) no or minimal dark areas (overlapped carriers), and/or (3) based on a suitable number of the carriers disposed towards the center of the well as opposed against an edge of the well. Carriers concentrated near side walls may be associated more often with increased numbers of overlaps. Also, the top and bottom of a well may constitute blind spots for an imaging system. In some cases, carriers in these regions cannot be imaged effectively by the system.

Tests were performed by swirling a microplate plate holding exemplary carriers (see Example 5) on an orbital shaker with various amounts of fluid in the well. Using a nine millimeter orbit, carriers were not dispersed suitably within the well, at speeds up to 450 rpm (maximum speed tested).

A "bumper" system on an orbital shaker may be used to disperse the exemplary carriers. Bumpers may be spaced such that a microplate coupled to the platform of the shaker is accelerated by orbital motion of the platform into one of the bumpers, thereby effecting a "strike" on the microplate (as with the finger tap method above). A "ring" or "rink" type approach may be used as an alternative to the bumpers. Either of these two approaches may perform a reasonable job of dispersing the carriers.

Dispersion may be provided by applying the same strike force on the microplate regardless of direction. In particular, if the force coming from a first set of strikes is greater than a second set of strikes coming from a different direction, the carriers may tend to orient in the direction of the stronger force. In some cases, it may be desirable to orient the carriers in this manner. The dispersion may be performed so that no substantial rotational motion of the microplate occurs during the strikes. Rotational motion during the strikes may cause the carriers to congregate to one side of a well, potentially leading to numerous carrier overlaps.

Dispersion may be performed with a dispersion apparatus. The apparatus may include a microplate holder attached to a rail (for example, an "x-rail"). The x-rail may be attached to a perpendicular rail (the "y-rail"). Movement along either rail may be efficient, bounded only by adjustable stops on each rail axis. The apparatus also may have an adjustable attachment device that allows the apparatus to be affixed to any orbital shaker that has a "flask attachment platform" accessory (a platform with a pattern of screw holes for attaching flask brackets). Most orbital shakers have such an accessory. The diameter of the orbit may affect dispersion.

When the apparatus described above is attached to a 19 mm stroke orbital shaker and operated at 200 to 350 rpm, exemplary carriers may be dispersed efficiently in a well of a microplate, such as a standard 96-well microplate. There may be no apparent breakage or loss of cells. The plate holder portion of the apparatus may be designed to allow the holder to tilt as the unit is subjected to the orbital motion, or the holder may the hold the microplate in a horizontal position.

The type of sample attached to the carriers may affect dispersion. For example, different cell types may change how readily the carriers are dispersed. Some cell types may be more "sticky" or more "slippery" than other cell types. This may affect the speed and time required to achieve acceptable dispersion. Furthermore, carriers without cells attached may disperse more readily (for example, at lower orbital speeds) than carriers with cells attached. The apparatus also or alternatively may be used to disperse carriers when they are placed on transfer platforms (ladles), such as in preparation for connection to samples (such as cells). In this case, a lower orbital speed may be used, such as about 100-125 rpm.

Orbital shakers come in various standard orbit sizes, with 8 and 19 mm orbits being used commonly. The dispersion apparatus was tested on each orbital shaker with the "run" of the X- and Y-axes set to either 8 mm or 15 mm. (The x-run was always equal to the y-run.) A 19 mm orbital shaker using the dispersion apparatus with 8 mm runs may disperse carriers efficiently. In some examples, this configuration may be about 30-40% more efficient than a 19 mm orbit coupled to 15 mm runs, and about 20% more efficient than a pairing of an 8 mm run with and 8 mm orbit. An 8 mm run as an optimum may be related to the inertia required to get the dispersion apparatus up to speed.

The 19 mm orbit/8 mm run may be efficient because the maximum speed in any direction of the orbit occurs when the velocity vector (tangent) of the orbit is in the same direction as the motion of the rails of the disperser. This alignment may occur when the orbit rotation is one-half way through its total motion in that direction (or one quarter of a complete turn; the first half of a rotation is in the to direction, the second half is in the fro direction.) However, the 8 mm orbital/8 mm runs may perform almost as well in some examples. Accordingly, optimum dispersion may be achieved by a combination of setting the run distance to that corresponding to maximal velocity, and an inertial factor required to get the bed of the disperser up to that speed.

Striking of the rail with a stop/bumper demarking the end of the rail run may be dampened to reduce the noise caused by the strikes. However, the material used to dampen the contacts advantageously may be hard itself, or may have high resiliency. In some examples, bumpers made of ¼ inch or less sorbothane polyurethane (hardness level of 40, which may be on the "soft" side of firm) may have suitable noise dampening properties (about 10-11 dB) while yielding good dispersing results. With the use of a rubber band to dampen the microtiter plate lid, and the use of sorbothane polyurethane bumpers, the noise production may be reduced to 57 dB from 74 dB in some cases.

Thin felt layers may be used in a dispersion apparatus to eliminate ringing of the upper platform. However, felt may be avoided near the rails to avoid stray threads of felt falling onto the rails and affecting the motion. In some examples, an orbital speed of 250 rpm for 30 seconds may yield very good dispersion, with about 80-100 or more exemplary carriers that are readable (dispersed effectively) per well.

Example 9

Exemplary Assay Systems

The example describes additional exemplary assay systems, including apparatus, methods, compositions, and kits, for preparing, positioning, treating, and/or analyzing samples, among others, in accordance with aspects of the present teachings. Preparing samples, as used here, may include, among others, (1) selecting, separating, enriching, growing, modifying, and/or synthesizing a composition, a cellular component, a cell, a tissue, and/or any other assay component, among others, (2) selecting, forming, and/or modifying sample carriers and/or sample containers, such as coded carriers and/or multiwell systems, respectively, and/or (3) associating samples and sample carriers, or mixtures thereof. Positioning samples, as used here, generally involves positioning the samples (and/or any associated sample carriers) for treatment and/or analysis, among others. Such positioning may include, among others, (1) mixing samples, (2) dispensing samples at treatment and/or analysis sites, and/or (3) dispersing samples at treatment and/or analysis sites, for example, to allow access to the samples and/or visualization of the samples, respectively. Treating samples, as used here, may include exposing the samples to some condition, such as a chemical, a temperature, a concentration (e.g., an ion concentration, such as hydrogen ion (pH), salt ion, etc.), and/or the like, and/or a change thereof. Analyzing the sample may include observing and/or measuring, qualitatively and/or quantitatively, a condition of the sample (e.g., size, mass, identity, etc.,) and/or a condition caused by the sample (e.g., depletion of an enzyme substrate, production of an enzyme product, etc.), using any suitable method(s) (e.g., optical (imaging, absorption, scattering, luminescence, photoluminescence (e.g., fluorescence or phosphorescence), chemiluminescence, etc.), magnetic resonance, and/or hydrodynamics, among others). Such analyzing further may include detecting and/or interpreting a presence, amount, and/or activity of the sample, or a modulator thereof, including agonists and/or antagonists, and/or determining trends or motifs from the analysis of multiple samples.

These exemplary systems are described in the following U.S. provisional patent applications, which are incorporated by reference in their entirety for all purposes: Ser. No. 60/523,747, filed Nov. 19, 2003; and Ser. No. 60/537,454, filed Jan. 15, 2004. These exemplary systems may be combined, optionally, with apparatus, methods, compositions, and/or kits, or components thereof, described elsewhere in this application and/or in the various patent applications listed above under Cross-References and incorporated herein by reference.

Example 10

Miscellaneous Considerations

This example describes additional aspects of the present teachings, including systems for dispensing, dispersing, and transferring particles, among others, presented as a series of numbered paragraphs.

1. A system for dispensing particles from a pile of particles in fluid, comprising (A) a dispenser including a tip portion and a loading mechanism configured to load the tip portion with a subset of the pile of particles; (B) a positioner that adjusts a relative vertical disposition of the particles and the tip portion; and (C) a controller configured to operate the positioner so that the tip portion is positioned automatically relative to, and based upon, an upper surface of a remaining portion of the pile of particles during each of a plurality of loading cycles performed by the loading mechanism.

2. The system of paragraph 1, wherein the dispenser is configured to move fluid through the tip portion, and wherein the tip portion defines a volume in which particles are retained during inflow of fluid.

3. The system of paragraph 2, wherein the tip portion includes a filter that permits flow of fluid and restricts movement of the particles, and wherein the filter defines a perimeter region of the volume.

4. The system of paragraph 1, wherein the dispenser includes a pump, and wherein the pump is configured to be operated by the controller to load the tip portion automatically.

5. The system of paragraph 1, wherein the positioner is configured to move the tip portion along a vertical axis.

6. The system of paragraph 1, further comprising a position sensor configured to sense a vertical proximity of the tip portion and the upper surface of the pile of particles.

7. The system of paragraph 6, the pile of particles being held by a vessel, wherein the position sensor is configured to sense the vertical proximity by sensing downward movement of the vessel.

8. The system of paragraph 1, the pile of particles being held by a vessel, the system further comprising a support structure for the vessel, wherein the support structure is configured to permit downward movement of the vessel in response to contact of the tip portion with the pile of particles.

9. The system of paragraph 1, further comprising a position sensor, wherein movement of the support structure is sensed by the position sensor.

10. The system of paragraph 1, wherein the controller is configured to operate the positioner based, at least in part, on the number of loading cycles already performed on the pile of particles.

11. The system of paragraph 10, further comprising a position sensor configured to sense a vertical proximity of the tip portion and the upper surface of the pile of particles, wherein the controller is configured to operate the positioner based, at least in part, on data from the position sensor.

12. The system of paragraph 1, wherein the positioner is configured to move the tip portion to a receiving site after the subset of the pile is loaded, and wherein the dispenser is configured to release at least a substantial portion of the subset at the receiving site.

13. The system of paragraph 1, wherein the controller is configured to operate the dispenser and the positioner so that subsets of the particles are dispensed to microplate wells.

14. The system of paragraph 13, wherein the controller is configured so that subsets of the particles can be dispensed automatically to a plurality of microplate wells from the pile of particles.

15. A method of dispensing particles, comprising (A) loading a tip portion of a dispenser with a predefined amount of particles from a pile of particles in fluid; (B) releasing, after loading, at least a substantial portion of the predefined amount of particles to a receiving site; and (C) repeating the steps of loading and releasing a plurality of times automatically to dispense subsets of the particles to different receiving sites.

16. The method of paragraph 15, wherein the step of loading loads the tip portion with an average number of particles that varies with a standard deviation of less than about one-half the average number.

17. The method of paragraph 15, further comprising a step of contacting the pile of particles with the tip portion before the step of loading.

18. The method of paragraph 17, wherein the step of contacting includes a step of moving the tip portion downward toward the pile of particles, and wherein the step of loading includes a step of drawing particles into the tip portion as the tip portion is raised from the pile of particles.

19. The method of paragraph 15, further comprising a step of moving at least one of the tip portion and the pile of particles to a vertical position before the step of loading, wherein the vertical position is based, at least partially, on the number of times that the steps of loading and releasing have been performed.

20. The method of paragraph 15, further comprising a step of automatically moving at least one of the tip portion and the particle supply to a vertical position before the step of loading for one or more of the plurality of times, wherein the vertical position is based, at least partially, on a sensed proximity of the tip portion and pile of particles.

21. A method of dispensing particles, comprising (A) placing a tip portion of a dispenser adjacent an upper surface of a pile of particles; (B) loading the tip portion with a subset of the pile of particles; (C) releasing at least a substantial portion of the subset of the pile to a receiving site; and (D) repeating the steps of placing, loading, and releasing a plurality of cycles automatically to dispense portions of the pile of particles to different receiving sites.

22. The method of paragraph 21, wherein the step of placing includes a step of moving at least one of the tip portion and the upper surface of the pile of particles to a vertical position, the vertical position being based on at least one of (a) the number of times the step of loading has been repeated, and (b) a sensed proximity of the tip portion and the upper surface during a present or earlier cycle.

23. The method of paragraph 21, wherein the step of loading includes a step of drawing fluid into the tip portion as the tip portion is moving away from the upper surface of the pile of particles.

24. The method of paragraph 21, wherein the step of placing includes a step of expelling fluid from the tip portion as the tip portion is moved toward the upper surface of the pile of particles.

25. The method of paragraph 21, wherein the step of loading is performed at a rate of fluid flow, and wherein the rate of fluid flow is decreased after loading is completed and before the top portion leaves the fluid in which the pile of particles is disposed.

26. The method of paragraph 25, wherein the rate of fluid flow into the tip portion is nonzero as the tip portion leaves the fluid.

27. A method of dispensing particles, comprising (A) loading a tip portion with particles from an upper surface of a pile of particles in fluid; (B) releasing at least a substantial portion of the particles to a receiving site; and (C) repeating the steps of loading, and releasing a plurality of cycles automatically to dispense portions of the pile of particles to different receiving sites.

28. A system for dispensing particles, comprising (A) means for loading a tip portion of a dispenser with a predefined amount of particles from a pile of particles in fluid; (B) means for releasing, after loading, at least a substantial portion of the predefined amount of particles to a receiving site; and (C) means for repeating the steps of loading and releasing a plurality of times automatically to dispense subsets of the particles to different receiving sites.

29. An apparatus for dispersion of particles, comprising (A) a holder for a vessel in which particles are disposed; (B) a base configured to be moved orbitally; and (C) a guide mechanism coupling the base slidably to the holder and configured to substantially restrict movement of the holder, relative to the base, to a plurality of linear segments, so that orbital motion of the base causes the vessel to travel along the linear segments and stop suddenly at ends thereof to disperse the particles.

30. The apparatus of paragraph 29, wherein the holder is configured to hold one or more microplates.

31. The apparatus of paragraph 29, wherein the base is configured to be secured to a platform of an orbital shaker.

32. The apparatus of paragraph 29, wherein the guide mechanism includes one or more stops configured to define the length and ends of each of the linear segments and to cause the vessel to stop suddenly at the ends.

33. The apparatus of paragraph 32, wherein the guide mechanism includes a pair of plates, and wherein the plates include wall regions configured to contact the one or more stops so that ends of the linear paths are defined.

34. The apparatus of paragraph 29, wherein the guide mechanism includes a pair of guide assemblies permitting linear motion of the holder, relative to the base, along orthogonal paths.

35. A method of particle dispersion, comprising (A) disposing particles in a vessel; (B) coupling the vessel to a member so that motion of the vessel relative to the member is restricted to a plurality of nonparallel linear segments; and (C) moving the member orbitally so that the vessel travels along the linear segments and stops suddenly at the ends thereof, thereby dispersing the particles.

36. The method of paragraph 35, wherein the step of disposing includes a step of disposing fluid in the vessel.

37. The method of paragraph 35, the vessel being a microplate having a plurality wells, wherein the step of moving disperses particles concurrently in two or more of the plurality of wells.

38. The method of paragraph 35, wherein the step of coupling the vessel to a member couples the vessel to a platform of an orbital shaker.

39. The method of paragraph 35, the linear segments each having a length, wherein the step of moving places the member in an orbit having a diameter that is approximately equal to or greater than the length of each linear segment.

40. The method of paragraph 35, wherein the step of moving causes the vessel to travel along linear segments having at least substantially the same length.

41. The method of paragraph 35, wherein the step of moving causes the vessel to travel along linear segments that are disposed orthogonally to one another.

42. The method of paragraph 35, wherein the step of moving the member orbitally includes setting an orbital rate of about 100 to 500 revolutions per minute.

43. An apparatus for dispersion of particles, comprising (A) means for coupling a vessel holding particles to a member so that motion of the vessel relative to the member is restricted to a plurality of nonparallel linear segments; and (B) means for moving the member orbitally so that the vessel travels along the linear segments and stops suddenly at the ends thereof, thereby dispersing the particles.

44. A device for transferring particles, comprising (A) a platform structure in a substantially sterile condition, the platform structure including a base and a wall joined to the base, the base having a support surface that is generally planar, the wall circumscribing the support surface to form a compartment with the base for retaining particles and defining an opening through which the particles can be released; and (B) a handle connected to the platform structure.

45. A system for connecting cells to particles, comprising (A) a vessel configured to hold fluid; and (B) a transfer platform including (i) a platform structure configured to be received in the vessel and including a base and a wall joined to the base, the base having a support surface for supporting particles, the wall circumscribing the support surface to form a compartment in which particles are retained during connection to cells, the wall having an opening through which the particles can be released, and (ii) a handle connected to the platform structure.

46. A method of transferring particles, comprising (A) contacting an assay material with particles disposed on a platform in a first vessel so that the assay material connects to the particles on the platform; (B) removing the platform from the first vessel, after the step of contacting and with the particles on the platform; and (C) transferring the particles into a second vessel from the platform after the step of removing.

47. The method of paragraph 46, wherein the step of contacting includes a step of contacting cells with particles.

48. The method of paragraph 46, further comprising a step of dispersing the particles on the platform.

49. The method of paragraph 46, wherein the step of contacting is performed with the platform immersed in fluid.

50. The method of paragraph 46, wherein the step of removing the platform includes a step of manually grasping a handle connected to the platform.

51. The method of paragraph 46, wherein the step of transferring includes a step of tilting the platform.

52. The method of paragraph 51, wherein the step of transferring includes a step of substantially inverting the platform.

53. The method of paragraph 46, wherein the step of transferring includes a step of contacting fluid on the platform with a funnel positioned to guide fluid into the second vessel, so that the fluid flows from the platform through the funnel and into the second vessel.

54. The method of paragraph 46, wherein the steps of contacting and removing are performed a plurality of times with distinct first vessels and distinct particles, and wherein the step of transferring is performed with the same second vessel for each of the plurality of times so that the distinct particles are placed together in the second vessel.

55. The method of paragraph 54, the assay material being cells, wherein the steps of contacting and removing are performed a plurality of times with different cells so that the step of placing places the different cells connected to distinct particles together in the second vessel.

56. A method of introducing particles to a particle mixture, comprising (A) placing particles on a transfer member; (B) connecting cells to the particles after the step of placing; and (C) tilting the transfer member after the step of connecting so that the particles fall off the transfer member and into or onto a receiver structure.

57. The method of paragraph 56, wherein the step of placing includes a step of placing particles on a generally planar surface of the transfer member.

58. The method of paragraph 56, wherein the step of placing includes forming a substantial monolayer of the particles.

59. The method of paragraph 56, wherein the step of connecting cells includes (i) a step of placing the transfer member in a vessel, and (ii) a step of dispensing the cells in fluid to the vessel.

60. The method of paragraph 59, the transfer member including a handle member, the method further comprising a step of removing the transfer member from the vessel after engagement with the handle member and before the step of tilting.

61. The method of paragraph 56, the transfer member including a support surface and a lip disposed adjacent a perimeter of the support surface, wherein the step of tilting includes a step of moving the particles past the lip.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A system for dispensing particles from a pile of particles in fluid, comprising:
    a dispenser including a tip portion and a loading mechanism configured to load the tip portion with a subset of the pile of particles;
    a positioner that adjusts a relative vertical disposition of the particles and the tip portion; and
    a controller configured to operate the positioner so that the tip portion is positioned automatically relative to, and based upon, an upper surface of a remaining portion of the pile of particles during each of a plurality of loading cycles performed by the loading mechanism.

2. The system of claim 1, wherein the dispenser is configured to move fluid through the tip portion, and wherein the tip portion defines a volume in which particles are retained during inflow of fluid.

3. The system of claim 2, wherein the tip portion includes a filter that permits flow of fluid and restricts movement of the particles, and wherein the filter defines a perimeter region of the volume.

4. The system of claim 1, wherein the dispenser includes a pump, and wherein the pump is configured to be operated by the controller to load the tip portion automatically.

5. The system of claim 1, wherein the positioner is configured to move the tip portion along a vertical axis.

6. The system of claim 1, further comprising a position sensor configured to sense a vertical proximity of the tip portion and the upper surface of the pile of particles.

7. The system of claim 6, the pile of particles being held by a vessel, wherein the position sensor is configured to sense the vertical proximity by sensing downward movement of the vessel.

8. The system of claim 1, the pile of particles being held by a vessel, the system further comprising a support structure for the vessel, wherein the support structure is configured to permit downward movement of the vessel in response to contact of the tip portion with the pile of particles.

9. The system of claim 8, further comprising a position sensor, wherein movement of the support structure is sensed by the position sensor.

10. The system of claim 1, wherein the controller is configured to operate the positioner based, at least in part, on the number of loading cycles already performed on the pile of particles.

11. The system of claim 10, further comprising a position sensor configured to sense a vertical proximity of the tip portion and the upper surface of the pile of particles, wherein the controller is configured to operate the positioner based, at least in part, on data from the position sensor.

12. The system of claim 1, wherein the positioner is configured to move the tip portion to a receiving site after the subset of the pile is loaded, and wherein the dispenser is configured to release at least a substantial portion of the subset at the receiving site.

13. The system of claim 1, wherein the controller is configured to operate the dispenser and the positioner so that subsets of the particles are dispensed to microplate wells.

14. The system of claim 13, wherein the controller is configured so that subsets of the particles can be dispensed automatically to a plurality of microplate wells from the pile of particles.

* * * * *